US012642611B2

(12) United States Patent
Saeidi et al.

(10) Patent No.: US 12,642,611 B2
(45) Date of Patent: Jun. 2, 2026

(54) METHOD AND SYSTEM FOR A CONFIDENCE-BASED SUPERVISED-AUTONOMOUS CONTROL STRATEGY FOR ROBOTIC-ASSISTED SURGERY

(71) Applicant: THE JOHNS HOPKINS UNIVERSITY, Baltimore, MD (US)

(72) Inventors: Hamed Saeidi, Wilmington, NC (US); Axel Krieger, Fulton, MD (US); Michael Kam, Baltimore, MD (US); Simon Leonard, State College, PA (US); Justin Opfermann, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 176 days.

(21) Appl. No.: 18/552,949

(22) PCT Filed: Mar. 28, 2022

(86) PCT No.: PCT/US2022/022193
§ 371 (c)(1),
(2) Date: Sep. 28, 2023

(87) PCT Pub. No.: WO2022/212284
PCT Pub. Date: Oct. 6, 2022

(65) Prior Publication Data
US 2024/0180646 A1     Jun. 6, 2024

Related U.S. Application Data

(60) Provisional application No. 63/167,452, filed on Mar. 29, 2021.

(51) Int. Cl.
*A61B 34/30*          (2016.01)
*A61B 17/06*          (2006.01)
(Continued)

(52) U.S. Cl.
CPC ........ *A61B 34/32* (2016.02); *A61B 17/06166* (2013.01); *A61B 34/10* (2016.02);
(Continued)

(58) Field of Classification Search
CPC ......... A61B 34/00; A61B 34/10; A61B 34/32; A61B 34/25; A61B 90/37; A61B 17/06166
See application file for complete search history.

(56) References Cited

U.S. PATENT DOCUMENTS

| | | |
|---|---|---|
| 2014/0127660 A1 | 5/2014 | Rappel et al. |
| 2017/0076450 A1 | 3/2017 | Sela et al. |

(Continued)

OTHER PUBLICATIONS

Lee, S. (Authorized officer), International Preliminary Report on Patentability in corresponding International Application No. PCT/US2022/022193 mailed on Oct. 12, 2023, 11 pages.

(Continued)

*Primary Examiner* — Vi X Nguyen
(74) *Attorney, Agent, or Firm* — MH2 Technology Law Group LLP

(57) ABSTRACT

A computer system, a computer-readable medium, and a computer-implemented method for robot-assisted suturing is disclosed. The computer-implemented method includes determining, by a suture planner algorithm executed by a hardware processor, a desired location for a suture for a potential suture location on a treatment area on a patient and determining which sutures from the suture planner algorithm can be done autonomously and which sutures may require human intervention to be performed.

16 Claims, 19 Drawing Sheets

(51) Int. Cl.

| | | |
|---|---|---|
| *A61B 34/00* | (2016.01) | |
| *A61B 34/10* | (2016.01) | |
| *A61B 34/32* | (2016.01) | |
| *A61B 90/00* | (2016.01) | |

(52) U.S. Cl.
CPC .............. *A61B 34/25* (2016.02); *A61B 90/37* (2016.02); *A61B 2034/107* (2016.02); *A61B 2090/371* (2016.02)

(56) References Cited

U.S. PATENT DOCUMENTS

| | | | |
|---|---|---|---|
| 2019/0282307 A1 | 9/2019 | Azizian et al. | |
| 2020/0022615 A1 | 1/2020 | Schoepp et al. | |
| 2020/0367974 A1* | 11/2020 | Khalid ................... | A61B 34/20 |
| 2021/0077195 A1* | 3/2021 | Saeidi ................... | A61B 34/10 |

OTHER PUBLICATIONS

Kim, H. (Authorized officer), International Search Report and Written Opinion in corresponding International Application No. PCT/US2022/022193 mailed on Jun. 9, 2022, 15 pages.

* cited by examiner

100

110

108

112

300

<table>
<tr>
<td>318<br>TRAJECTORY<br>GENERATOR</td>
<td>320<br>INVERSE<br>KINEMATICS<br>(OROCOCS-KDL)</td>
<td>322<br>LOW-LEVEL<br>CONTROLLER<br>(FRI & OROCOS-RTT)</td>
<td>324<br>ROBOT</td>
</tr>
</table>

POSITION FEEDBACK

326

314

<table>
<tr>
<td>316<br>HIGH-LEVEL<br>SUTURING<br>LOGIC</td>
<td>REF<br><br>POINTS</td>
<td>310<br>CONFIDENCE<br>BASED<br>ALLOCATION</td>
<td>A</td>
<td>308<br>SUTURE<br>PLANNER<br>(24)</td>
<td>304<br>NIR CAM<br><br>RGBD CAM</td>
<td>302<br>TEST<br>SAMPLE</td>
</tr>
</table>

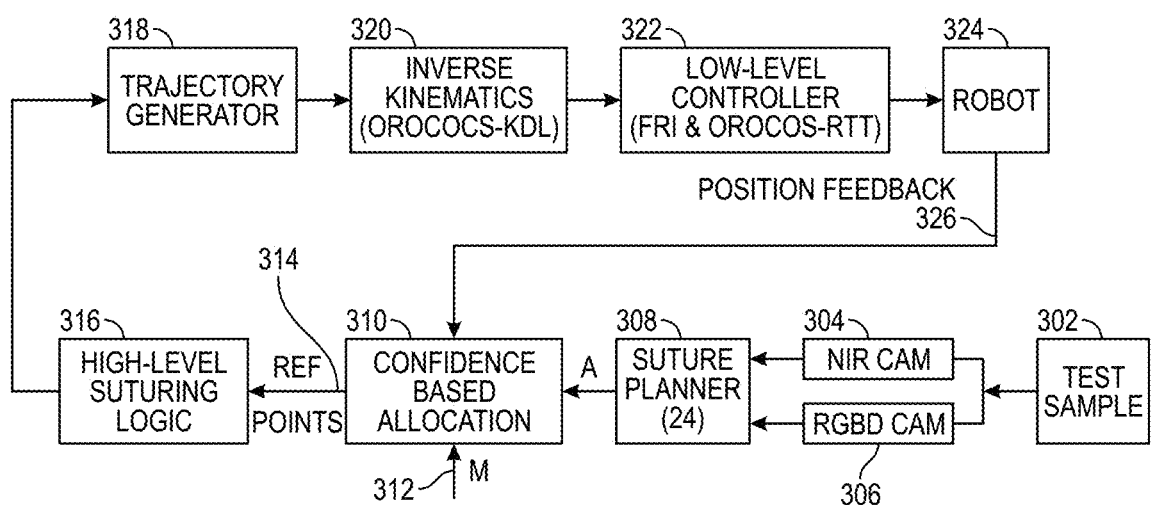

Autonomous plans on low-density sensor data. Teleoperation is more accurate.

Autonomous plans on high-density sensor data. Autonomous control is more accurate Side view of the 3D surface of the target tissue. Incision plan waypoints are shown via blue spheres.

Suggested Mode:    — Auto    — Teleop
Current Mode: Teleop

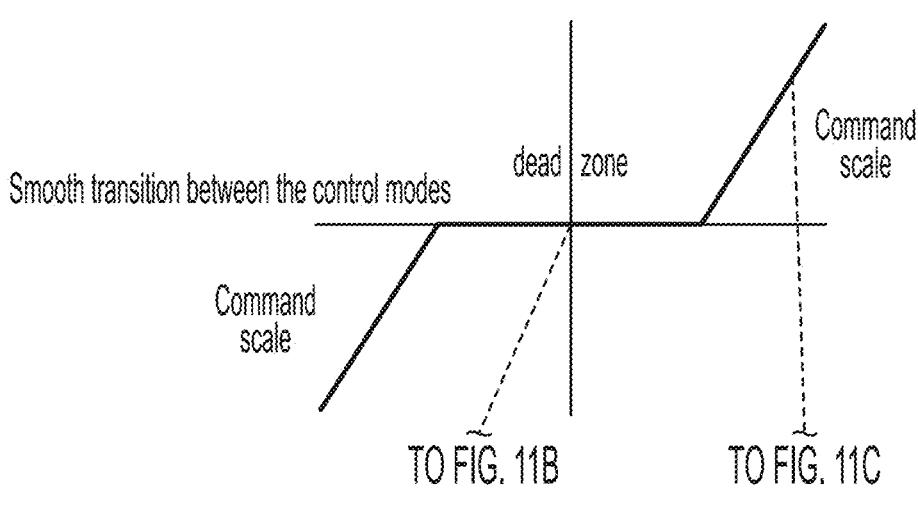
FIG. 11A
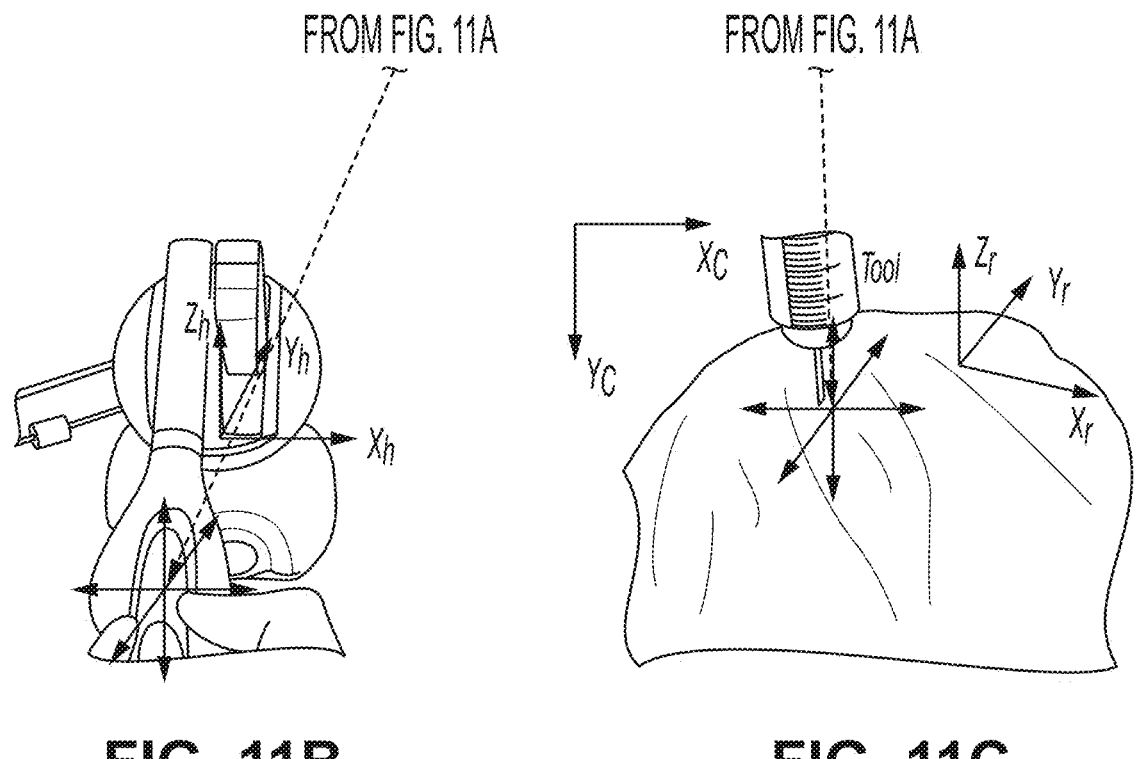
FIG. 11B          FIG. 11C

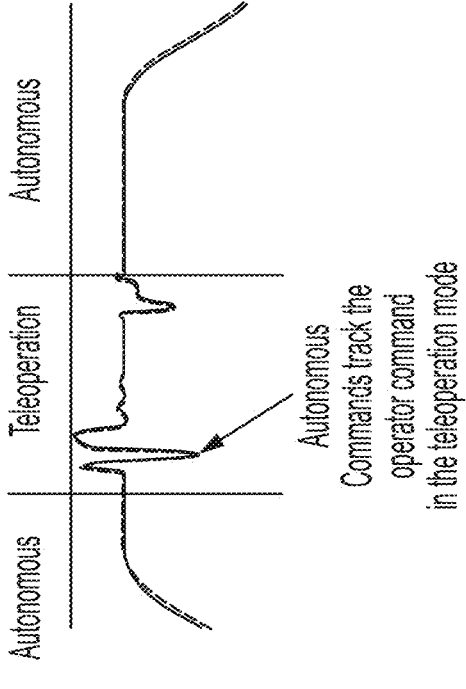

Autonomous     Teleoperation     Autonomous

Autonomous Commands track the operator command in the teleoperation mode

An example of autonomous trajectories during teleoperation when tracking the operator commands (which enables smooth transitions from teleoperation to autonomous control).

FIG. 12B

Autonomous     Teleoperation     Autonomous

Robot position resulted from teleoperation commands

Autonomous commands (ready to engage after teleoperation)

An example of autonomous trajectories during teleoperation without tracking the operator commands (which causes non-smooth transitions from teleoperation to autonomous control).

FIG. 12A

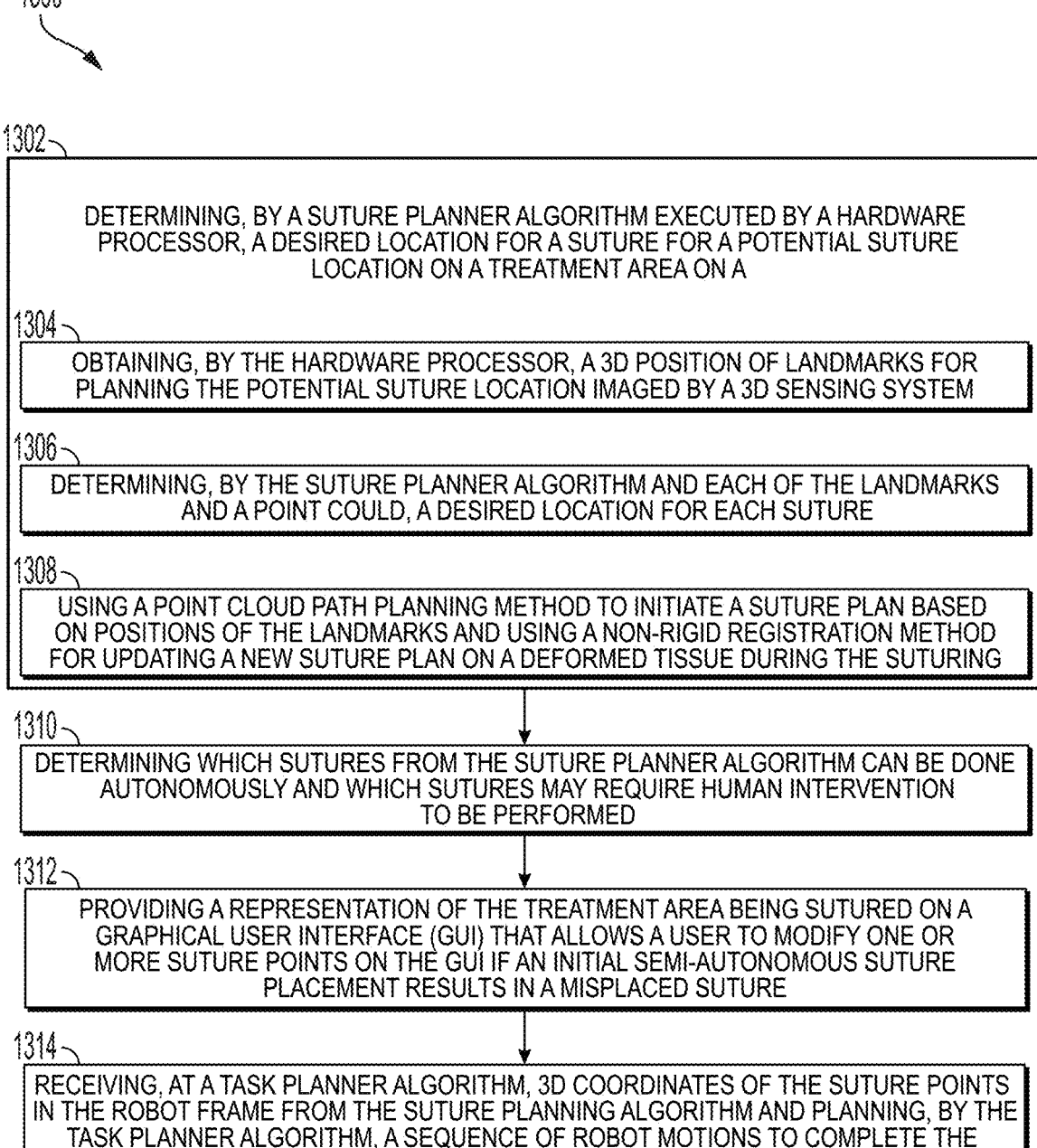

1300

1302
DETERMINING, BY A SUTURE PLANNER ALGORITHM EXECUTED BY A HARDWARE PROCESSOR, A DESIRED LOCATION FOR A SUTURE FOR A POTENTIAL SUTURE LOCATION ON A TREATMENT AREA ON A

1304
OBTAINING, BY THE HARDWARE PROCESSOR, A 3D POSITION OF LANDMARKS FOR PLANNING THE POTENTIAL SUTURE LOCATION IMAGED BY A 3D SENSING SYSTEM

1306
DETERMINING, BY THE SUTURE PLANNER ALGORITHM AND EACH OF THE LANDMARKS AND A POINT COULD, A DESIRED LOCATION FOR EACH SUTURE

1308
USING A POINT CLOUD PATH PLANNING METHOD TO INITIATE A SUTURE PLAN BASED ON POSITIONS OF THE LANDMARKS AND USING A NON-RIGID REGISTRATION METHOD FOR UPDATING A NEW SUTURE PLAN ON A DEFORMED TISSUE DURING THE SUTURING

1310
DETERMINING WHICH SUTURES FROM THE SUTURE PLANNER ALGORITHM CAN BE DONE AUTONOMOUSLY AND WHICH SUTURES MAY REQUIRE HUMAN INTERVENTION TO BE PERFORMED

1312
PROVIDING A REPRESENTATION OF THE TREATMENT AREA BEING SUTURED ON A GRAPHICAL USER INTERFACE (GUI) THAT ALLOWS A USER TO MODIFY ONE OR MORE SUTURE POINTS ON THE GUI IF AN INITIAL SEMI-AUTONOMOUS SUTURE PLACEMENT RESULTS IN A MISPLACED SUTURE

1314
RECEIVING, AT A TASK PLANNER ALGORITHM, 3D COORDINATES OF THE SUTURE POINTS IN THE ROBOT FRAME FROM THE SUTURE PLANNING ALGORITHM AND PLANNING, BY THE TASK PLANNER ALGORITHM, A SEQUENCE OF ROBOT MOTIONS TO COMPLETE THE SUTURING USING DESIRED AND PLANNED POSITIONS

FIG. 13

METHOD AND SYSTEM FOR A CONFIDENCE-BASED SUPERVISED-AUTONOMOUS CONTROL STRATEGY FOR ROBOTIC-ASSISTED SURGERY

CROSS-REFERENCE TO RELATED APPLICATIONS

This application is the national stage entry of International Patent Application No. PCT/US2022/022193, filed on Mar. 28, 2022, and published as WO 2022/212284 A1 on Oct. 6, 2022, which claims the benefit of U.S. Provisional Patent Application Ser. No. 63/167,452, filed Mar. 29, 2021, both of which are hereby incorporated by reference herein in their entireties.

GOVERNMENT RIGHTS

This disclosure was made with Government support under Grant Nos. 1R01EB020610 and R21EB024707 awarded by the National Institute of Biomedical Imaging and Bioengineering of the National Institutes of Health. The Government has certain rights in the invention.

FIELD

This disclosure relates generally robot-assisted surgery, and in particular, to a method and system for confidence-based supervised-autonomous control strategy for robot-assisted surgery.

BACKGROUND

Autonomous robotic suturing has the potential to improve surgery outcomes by leveraging accuracy, repeatability, and consistency compared to manual operations. However, achieving full autonomy in complex surgical environments is not practical and human supervision is required to guarantee safety. Robot-Assisted Minimally Invasive Surgery (RAMIS) systems take advantage of highly dexterous tools, hand tremor motion filtering and scaling to improve patient outcomes by reducing patient recovery times and collateral damage. However, majority of state-of-the-art systems for robotic assisted surgeries are based on a tele-operated paradigm. As an example, the pioneer and commercially successful da Vinci Surgical System (Intuitive Surgical, Sunnyvale, California) has been utilized in a wide range of surgical procedures in urology, cardiothoracic, and general surgery. Raven surgical robot developed at the University of Washington and Senhance system from Asenus Surgical (Morrisville, NC) are other examples of tele-operated systems.

Autonomous control algorithms for RAMIS benefit from robotic accuracy and repeatability during surgical procedures. Such systems possess the potential to reduce human errors, deliver improved patient outcomes independent of surgeon's training and experience, and also allow remote surgeries without high-bandwidth networks. Pre-planned autonomous RAMIS was implemented in bony orthopedic procedures (e.g., ROBODOC, Caspar, and CRIGOS), radiotherapy, and cochlear implants. Efforts in automating deformable and unstructured soft tissue surgeries include knot tying, needle insertion, deformable tissue tracking, and executing predefined motions. Machine learning techniques were introduced in robotic suturing to facilitate system calibration and to imitate surgical suturing from video demonstrations. However, achieving full autonomy in complex surgical environments is not infallible and surgeon supervision and control take over is useful for safe operation.

What is needed is an improved strategy for robot-assisted surgery that overcomes the above-noted issues.

SUMMARY

In accordance with examples of the present disclosure, a computer-implemented method for robot-assisted surgery is disclosed. The computer-implemented method comprises determining, by a suture planner algorithm executed by a hardware processor, a desired location for a suture for a potential suture location on a treatment area on a patient; and determining which sutures from the suture planner algorithm can be done autonomously and which sutures may require human intervention to be performed.

Various additional features can be included in the computer-implemented method including one or more of the following features. The determining the desired location comprises obtaining, by the hardware processor, a 3D position of landmarks for planning the potential suture location imaged by a 3D sensing system. The computer-implemented method further comprises determining, by the suture planner algorithm and each of the landmarks and a point could, a desired location for each suture. The computer-implemented method further comprises providing a representation of the treatment area being sutured on a graphical user interface (GUI) that allows a user to modify one or more suture points on the GUI, by textual input on the GUI, or by a haptic user interface if an initial semi-autonomous suture placement results in a misplaced suture. The computer-implemented method further comprises receiving, at a task planner algorithm, 3D coordinates of the suture points in the robot frame from the suture planning algorithm and planning, by the task planner algorithm, a sequence of robot motions to complete the suturing using desired and planned positions. The desired location of one or more sutures points are modifiable by activation of a graphical selection tool on a graphical user interface (GUI). The graphical selection tool comprises a slider, a pointer, a button, a multi-axis master control device, or combinations thereof. The one or more sutures points are color-coded on the GUI. The determining the desired location for suture comprises using a point cloud path planning method to initiate a suture plan based on positions of the landmarks and using a non-rigid registration method for updating a new suture plan on a deformed tissue during the suturing. The sequence of robot motions comprises motions representing approaching tissue at the treatment area, motions representing biting or firing a needle, motions representing tensioning the suture, or motions representing releasing the suture.

In accordance with examples of the present disclosure, a computer system is disclosed. The computer system comprises a hardware processor; a non-transitory computer readable medium comprising instructions that when executed by the hardware processor perform a method for robot-assisted surgery, the computer-implemented method comprising: determining, by a suture planner algorithm executed by a hardware processor, a desired location for a suture for a potential suture location on a treatment area on a patient; and determining which sutures from the suture planner algorithm can be done autonomously and which sutures may require human intervention to be performed.

Various additional features can be included in the computer system including one or more of the following features. The determining the desired location comprises obtaining, by the hardware processor, a 3D position of landmarks for planning the potential suture location imaged by a 3D sensing system. The method further comprises determining, by the suture planner algorithm and each of the landmarks and a point could, a desired location for each suture. The method further comprises providing a representation of the treatment area being sutured on a graphical user interface (GUI) that allows a user to modify one or more suture points on the GUI, by textual input on the GUI, or by a haptic user interface if an initial semi-autonomous suture placement results in a misplaced suture. The method further comprises receiving, at a task planner algorithm, 3D coordinates of the suture points in the robot frame from the suture planning algorithm and planning, by the task planner algorithm, a sequence of robot motions to complete the suturing using desired and planned positions. The desired location of one or more sutures points are modifiable by activation of a graphical selection tool on a graphical user interface (GUI). The graphical selection tool comprises a slider, a pointer, a button, a multi-axis master control device, or combinations thereof. The one or more sutures points are color-coded on the GUI. The determining the desired location for suture comprises using a point cloud path planning method to initiate a suture plan based on positions of the landmarks and using a non-rigid registration method for updating a new suture plan on a deformed tissue during the suturing. The sequence of robot motions comprises motions representing approaching tissue at the treatment area, motions representing biting or firing a needle, motions representing tensioning the suture, or motions representing releasing the suture.

In accordance with examples of the present teachings, a non-transitory computer readable medium comprising instructions that when executed by a hardware processor perform a method for robot-assisted suturing is disclosed. The computer-implemented method comprises determining, by a suture planner algorithm executed by a hardware processor, a desired location for a suture for a potential suture location on a treatment area on a patient; and determining which sutures from the suture planner algorithm can be done autonomously and which sutures may require human intervention to be performed.

Various additional features can be included in the non-transitory computer readable medium including one or more of the following features. The determining the desired location comprises obtaining, by the hardware processor, a 3D position of landmarks for planning the potential suture location imaged by a 3D sensing system. The computer-implemented method further comprises determining, by the suture planner algorithm and each of the landmarks and a point could, a desired location for each suture. The computer-implemented method further comprises providing a representation of the treatment area being sutured on a graphical user interface (GUI) that allows a user to modify one or more suture points on the GUI if an initial semi-autonomous suture placement results in a misplaced suture. The computer-implemented method further comprises receiving, at a task planner algorithm, 3D coordinates of the suture points in the robot frame from the suture planning algorithm and planning, by the task planner algorithm, a sequence of robot motions to complete the suturing using desired and planned positions. The desired location of one or more sutures points are modifiable by activation of a graphical selection tool on a graphical user interface (GUI). The graphical selection tool comprises a slider, a pointer, a button, a multi-axis master control device, or combinations thereof. The one or more sutures points are color-coded on the GUI. The determining the desired location for suture comprises using a point cloud path planning method to initiate a suture plan based on positions of the landmarks and using a non-rigid registration method for updating a new suture plan on a deformed tissue during the suturing. The sequence of robot motions comprises motions representing approaching tissue at the treatment area, motions representing biting or firing a needle, motions representing tensioning the suture, or motions representing releasing the suture.

In accordance with examples of the present disclosure, a computer-implemented method for robot-assisted suturing is disclosed The computer-implemented method comprises obtaining, by a hardware processor, a 3D position for one or more markers or landmarks on the tissue, such as one or more near infrared (NIR) markers, representing a potential suture location on a treatment area on a patient imaged by a dual-camera system, wherein the dual-camera system comprises a 3D visible color camera and a NIR camera; determining, by a suture planner algorithm and the one or more markers or landmarks and a point could, a desired location for each knot and running stitch; determining which sutures from the suture planner algorithm can be done autonomously and which sutures may require human intervention to be performed; providing a representation of the treatment area being sutured on a graphical user interface (GUI) that allows a user to modify one or more suture points on the GUI, by textual input on the GUI, or by a haptic user interface if the initial semi-autonomous suture placement results in a misplaced suture; receiving, at a task planner algorithm, 3D coordinates of the suture points in the robot frame from the suture planning algorithm; and planning, by the task planner algorithm, a sequence of robot motions to complete the suturing using desired and equally spaced positions.

Various additional features can be included in the computer-implemented method including one or more of the following features. The one or more sutures points are modifiable by activation of a graphical selection tool on the GUI. The graphical selection tool comprises a slider, a pointer, a button, or combinations thereof. The one or more sutures points are color-coded on the GUI. The suturing comprises any type of suture, such as a knot and running stitch. The determining the desired location for each knot and the running stitch comprises using a point cloud path planning method to initiate a suture plan based on positions of the one or more markers or landmarks and using a non-rigid registration method for updating a new suture plan on a deformed tissue during the suturing. The sequence of robot motions comprises motions representing approaching tissue at the treatment area, motions representing biting or firing a needle, motions representing tensioning the suture, or motions representing releasing the suture.

BRIEF DESCRIPTION OF THE FIGURES

Various features of the embodiments can be more fully appreciated, as the same become better understood with reference to the following detailed description of the embodiments when considered in connection with the accompanying figures, in which:

FIG. 3 shows an autonomous control loop with confidence-based manual adjustments according to examples of the present teachings.

FIG. 4A, FIG. 4B, FIG. 4C, FIG. 4D, FIG. 4E, FIG. 4F, FIG. 4G, FIG. 4H, and FIG. 4I show examples of reaching suture points on a phantom vaginal cuff and steps of the data collection, according to examples of the present teachings, where FIG. 4A shows point cloud view with three suture points selected, FIG. 4B shows a suture point is on an edge, FIG. 4C shows a suture point has a high chance to be caught, FIG. 4D shows a suture point has no chance to be caught, FIG. 4E shows a good orientation of a tool-tip to reach suture points, FIG. 4F shows a bad orientation of the tool-tip to reach suture points, FIG. 4G shows rectangular box model of tool-tip, FIG. 4H shows the projected rectangular box containing Point-on-Tool (POT) (points 404) and PIJ (points 406 to collect data on multiple suture points, and FIG. 4I shows projected rectangular boxes to collect data on multiple suture points.

In FIG. 5A, data point examples of a.I) high POT but low PIJ, a.II) high POT and high PIJ, a.III) low POT but high PIJ, and a.IV) no POT and no PIJ. FIG. 5B shows the confidence model identified for the hit/miss based on collected data.

FIG. 6A shows STAR, FIG. 6B shows manual, FIG. 6C shows a higher number of suture points before suturing, and FIG. 6D shows a lower number of suture points after the vaginal cuff is closed.

FIG. 11A, FIG. 11B, and FIG. 11C show smooth transitions between control modes according to examples of the present disclosure.

FIG. 12A and FIG. 12B show additional examples of smooth transitions between control modes according to examples of the present disclosure.

FIG. 13 shows a flowchart for a computer-implemented method for robot-assisted suturing, according to examples of the present teachings.

DETAILED DESCRIPTION

Figures 1A, 1B:
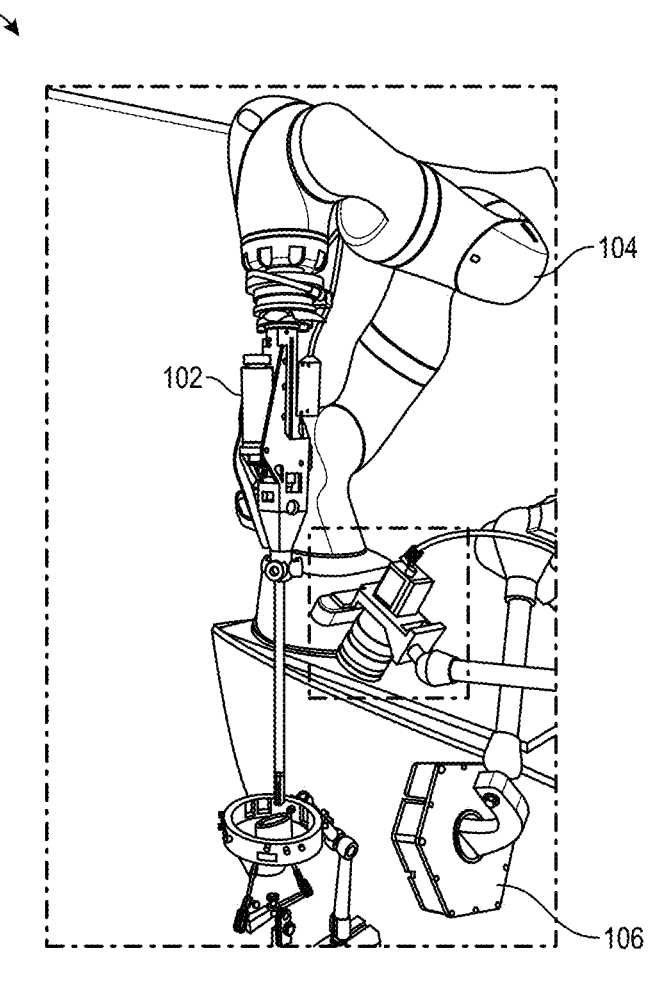
FIG. 1A shows an experiment setup for confidence-based supervised autonomous vaginal cuff closure.
FIG. 1B shows a dual camera system.

Reference will now be made in detail to example implementations, illustrated in the accompanying drawings. Wherever possible, the same reference numbers will be used throughout the drawings to refer to the same or like parts. In the following description, reference is made to the accompanying drawings that form a part thereof, and in which is shown by way of illustration specific exemplary embodiments in which the invention may be practiced. These embodiments are described in sufficient detail to enable those skilled in the art to practice the invention and it is to be understood that other embodiments may be utilized and that changes may be made without departing from the scope of the invention. The following description is, therefore, merely exemplary.

According to examples of the present disclosure, a confidence-based supervised autonomous suturing method is described to perform robotic suturing tasks via both Smart Tissue Autonomous Robot (STAR) and surgeon collaboratively with the highest possible degree of autonomy. Via the disclosed method, STAR performs autonomous suturing when highly confident and otherwise asks the operator for possible assistance in suture positioning adjustments. As described below, the accuracy of the disclosed control method was evaluated via robotic suturing tests on synthetic vaginal cuff tissues and compare them to the results of vaginal cuff closures performed by an experienced surgeon. However, this is merely one example application of the present disclosure. The is disclosed system and method can be applied in a wide variety of other supervised autonomous suturing methods as well. The test results indicate that by using the disclosed confidence-based method, STAR can predict the success of pure autonomous suture placement with an accuracy of 94.74%. Moreover, via an additional 25% human intervention, STAR can achieve a 98.1% suture placement accuracy compared to an 85.4% accuracy of completely autonomous robotic suturing. Finally, the experiment results indicate that STAR using the disclosed method achieves 1.6 times better consistency in suture spacing and 1.8 times better consistency in suture bite sizes than the manual results.

The disclosed supervised-autonomous control strategy that enables performing complex surgical procedures via both autonomous robot and surgeon collaboratively with the highest possible degree of autonomy, while ensuring safe operations. Thus, one element in achieving this objective effectively is designing algorithms that will make the autonomous robot "self-aware" of the limitations of its automation capabilities. Such algorithms innovate by maximizing the level of automation of the RAMIS and minimizing the expected errors of the variables for which the robot is confident of performing more accurately than its human supervisor via an effective collaboration between the two.

Collaborative control strategies take the general form $$U(t) = \alpha(t)M(t) + (1 - \alpha(t))A(t), \tag{1}$$

where M(t) are the manual control commands from a human operator that are combined with the autonomous control commands A(t) via complementary scales $\alpha(t) \in [0, 1]$ and $1 - \alpha(t)$ respectively in order to control the robot via the total control input U(t). Typical examples of such control inputs include position and velocity profiles, and force/torque.

Based on the application, different methods have been proposed for defining the function α(t). The goal is to determine α(t) dynamically based on an independent variable while the robotic control task is on the fly to fulfill certain performance criteria. Some examples include, dynamically changing α(t) based on position tracking accuracy, proximity to obstacles and/or desired locations, the prediction of human intentions in controlling the robot, and the trust of human to the autonomous controller of robot. In surgical applications, the robot autonomously constrains the roll-pitch-yaw motion of the surgical tool for precision drilling by the surgeon or for avoiding collisions, joint limits, and singularities. Shared autonomy has also been proven effective for reducing the complexity of steering flexible robotic endoscopes and flexible surgical manipulators. Such techniques have been utilized for improving the tissue cutting precision of surgical robots.

Generally speaking, a "self-aware" confidence-based strategy for robotic suturing is disclosed, with one non-limiting application example in vaginal cuff closure. In the disclosed method, the robotic system generates a suture plan and continuously tracks tissue deformations as common disturbances during surgery to update the produced plan. However, the system dynamically assesses the confidence levels in completing each step of the suturing process autonomously (based on tissue deformation) and suggests to the operators to intervene and fine-tune a suture point location if it is not feasible for the robot to complete that specific suture purely autonomous. The disclosed method takes advantage of human supervision to reduce the chance of sporadic autonomous control mistakes specially when the robot has to complete a long task in pure autonomous mode. This method can also provide an easier path towards regulatory approvals for the resulting RAMIS. In summary, this present disclosure describes: i) developing a confidence-based supervised control strategy for robotic suturing tasks, ii) assessing the performances of the autonomous control resource and identifying the confidence models for robot as well as the confidence-based allocation function α(t), and iii) experimentally evaluating the accuracy of the disclosed control strategy via multiple tests on synthetic vaginal cuff models and comparing them with pure manual vaginal cuff closures.

Figure 1C:
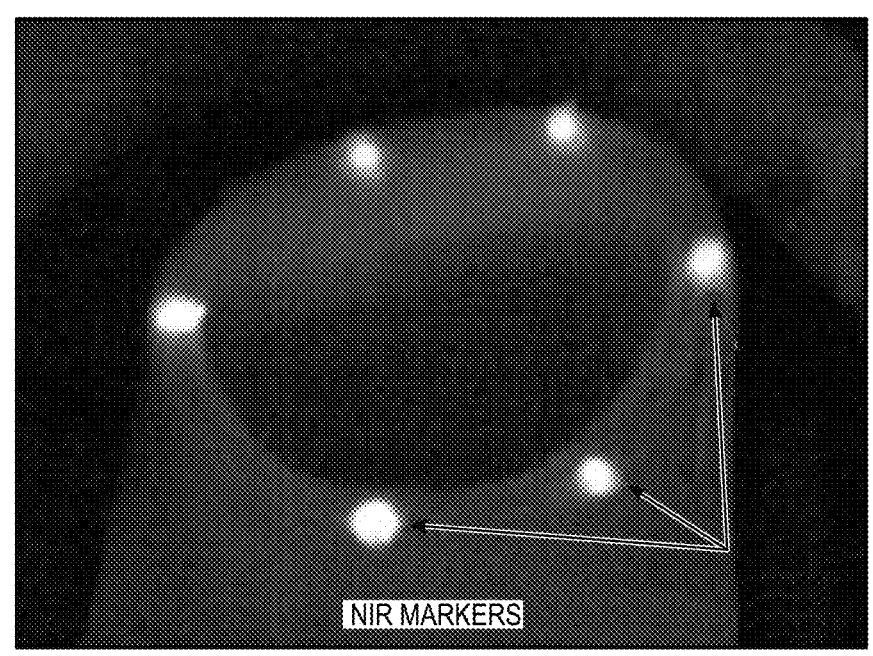
FIG. 1C shows a NIR image view with NIR markers on the vaginal cuff phantom.
Figure 1D:
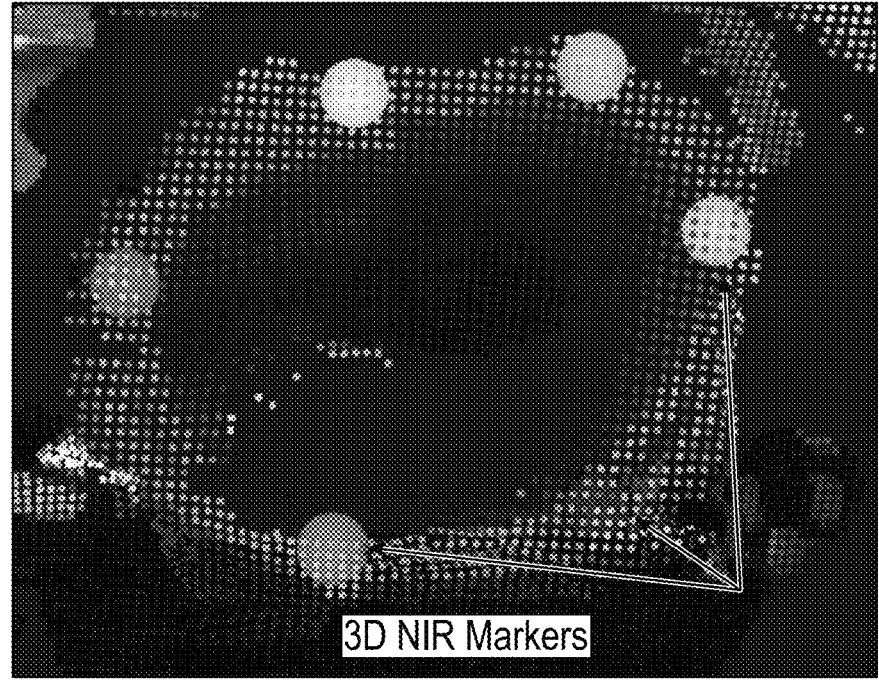
FIG. 1D shows a point cloud view from RGBD camera with 3D NIR marker overlaid, all according to examples of the present teachings.

FIG. 1A shows a system 100 for confidence-based supervised autonomous robot-assisted surgical procedure, such as a vaginal cuff closure, FIG. 1B shows a dual camera system, FIG. 1C shows a NIR image view with landmarks, e.g., one or more markers or landmarks, such as NIR markers, on the vaginal cuff phantom, and FIG. 1D shows a point cloud view from RGBD camera with 3D markers, such a NIR markers, overlaid, all according to examples of the present teachings. As shown in FIG. 1A, the system 100 comprises a laparoscopic suturing tool 102, such as a commercial Endo360° suturing device from EndoEvolution (North Chelmsford, MA, USA, and a robotic arm 104, such as a 7-DOF KUKA LBR Med lightweight arm (KUKA AG, Augsburg Germany), that is used to perform the suturing tasks. The system 100 also comprises a light source 106 and a 3D sensing system, such as a dual camera system 108. The system 100 can be modified by adding two DC brush motors (Maxon Motors, Sachseln, Switzerland) to drive a circular needle and control a pitch rotation of the tool tip. EPOS2 controllers (Maxon Motors, Sachseln, Switzerland) were used for precise positioning control, and were connected into a host computer using a controller area network (CAN). A multi-axis force sensor (ATI industrial automation, NC, USA) was used to measure the tensioning force to prevent tissue from damage during suturing tasks.

In one example, the dual camera imaging system 108, as shown in FIG. 1B comprises a 3D RGBD camera 110, such as a Realsense D415 (Intel Corp., Santa Clara, California) and a NIR camera 112, such as a 845 nm±55 nm 2D NIR camera (Basler Inc., Exton, PA). Generally speaking, any 3D camera system that detects landmarks on the target tissue can be used. The 3D camera detects 3D tissue surface information and the 2D Near-infrared (NIR) camera detects the location of NIR markers 116, as shown in FIG. 1C. In the experiments performed by the inventors, a light source with 760 nm light-emitting diode (North Coast Technical Inc., Chesterland, OH) was used to excite the fluorophore, enabling the NIR markers 116 to be visualized with the NIR camera 112, shown in FIG. 1C. The coordinate system of the 2D NIR image was registered to that of 3D camera through camera calibration. The 3D position of the NIR markers can be found by ray tracing the NIR marker 116 positions via a co-registered point cloud from the 3D camera 110, shown with points in FIG. 1D. A hand-eye calibration registered the 3D camera coordinate system onto the robot coordinate system by using a calibration rod and a checkerboard. The 3D location of the markers with respect to robot frame were obtained and used by STAR for suturing tasks.

In previous studies conducted by the inventors, the Near-infrared florescent (NIRF) marking technique plays a key role to enable the 3D vision tracking system to successfully track markers location. NIR markers have high signal to noise ratio (SNR) and strong signal penetration to improve target detection from background even under obstruction of blood and tissue, and therefore are suitable for intra-operative robot guidance. The spatial locations of NIR markers are extracted by a dual camera system and can be utilized for vision-guidance tasks.

According to examples of the present disclosure, a STAR is used to perform vaginal cuff closure on synthetic vaginal cuff tissue (3-Dmed, Ohio, United States). Synthetic tissue, with 5 cm diameter and 5 mm wall thickness, was chosen since it is designed for surgical training in vaginal cuff closure. The test samples were fastened within a 3D printed ring with two stay sutures coming from the side and two alligator clips clamping sample's edge from the bottom to simulate the clinical scenario including the attachment of the vaginal cuff to surrounding tissue. The test sample with the 3D printed ring was placed in front of the dual camera system with distance of 35-38 cm which satisfies the minimum sensing distance of the camera. NIR markers were manually placed on the cross-section edge of the tissue prior to the suturing task. The suturing results performed by STAR were compared to manual results of the previous study conducted by the inventors on i) total time to complete, ii) suture spacing (i.e. the distance between consecutive stitches), and iii) bite size (i.e. distance from where a stitch enters into tissue to the tissue surface). The latter two measures are relevant to post-surgical complications such as infection and dehiscence. Statistical analysis including T-test and Levene's test were utilized to compare averages and variances, respectively, for the evaluation criteria. Furthermore, to compare the new confidence-based method with pure autonomous control, the number of hit and misses (correct/incorrect suture placements) and the percentage of human intervention were compared.

Figure 2:
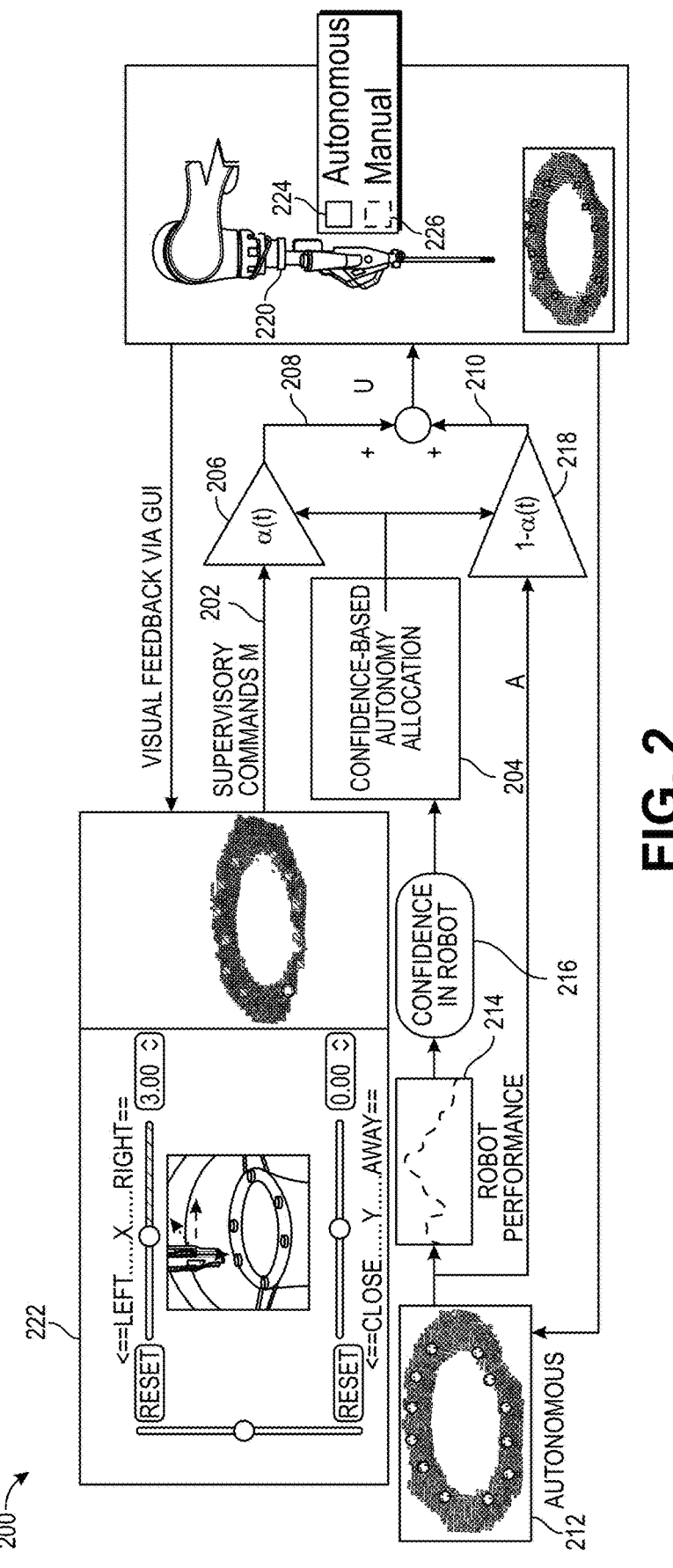
FIG. 2 shows a block diagram of a confidence-based supervised autonomous suturing method according to examples of the present teachings.

FIG. 2 shows a block diagram 200 of a confidence-based supervised autonomous suturing method according to examples of the present teachings. Supervisory commands M 202 and confidence-based autonomy allocation commands 204 are provided to an α(t) operator 206, which outputs 208 to produce the total output U. Autonomous 212 is evaluated to determine robot performance 214. The output of robot performance 214 is provided to confidence in robot 216 for calculating the confidence in robot. The output of the confidence in robot 216 is provided to the confidence-based autonomy allocation commands 204. The output of confidence-based autonomy allocation command 204 is provided to the α(t) operator 206 and a 1–α(t) operator 218. The addition operator 210 receives both the outputs of the α(t) operator 206 and a 1–α(t) operator 218 and produces an output to the robot 220. The robot 220 provides a feed-back to the autonomous 212 and provides visual feedback via a GUI 222.

FIG. 3 shows a block diagram 300 for an autonomous control loop with confidence-based manual adjustments according to examples of the present teachings. As shown in FIG. 3, the test sample 302 is imaged by both the NIR camera 304 and the RGBD camera 306. The outputs of the NIR camera 304 and the RGBD camera 306 are provided to a suture planner 308. The suture planner 308 uses the NIR markers 116 and the point cloud to determine the desired location of a suture, such as each knot and running stitch. The suture planner 308 incorporates a planning method developed in previous work of the inventors comprising a point cloud path planning method to initialize a suture plan based on the NIR marker positions followed by a non-rigid registration method for updating a new suture plan on a deformed tissue during the suturing steps. This includes producing an initial suture plan between the NIR markers on the tissue and registering them in a non-rigid deformation algorithm which will be used after each completing each stitch to update the new suture point locations based on the deformations detected from the NIR marker. The suture planner 308 outputs A to the confidence-based allocation unit 310. The confidence-based allocation unit 310 also receives M 312 and output reference points 314. The reference points 314 are provided to a high-level suturing logic unit 316. The output of the high-level suturing logic unit 316 is provided to a trajectory generator 318. The output of trajectory generator 318 is provided to an inverse kinematic (OROCOS-KDL) unit 320. The output of the inverse kinematic (OROCOS-KDL) unit 320 is provided to a low-level controller (FRI & OROCOS-RTT) 322. The low-level controller (FRI & OROCOS-RTT) 322 is provided to the robot 324. The robot 324 provides positional feedback information 326 to the confidence-based allocation unit 310.

The confidence-based allocation subsystem determines which sutures from the suture planner can be done autonomously and which ones will require a possible human intervention. In the GUI (shown in FIG. 2), autonomous suture points are highlighted in at 224 and manually adjusted points highlighted in by points 226. The user modifies the suture point location via slider bars in 3 dimensions if the initial semi-autonomous suture placement attempt for the points 226 results in a misplaced suture. Thus, operator supervises the robot when manual mode with α=1 is selected (also referred to as assisted mode here) and only modifies the target suture point location if needed.

Finally, a high-level suturing logic and task planner then receives the resulting 3D coordinates of the suture points in the robot frame and plans the sequence of robot motions to complete the suture, such as the knot and running stitches, on the desired positions. This includes a combination of approaching the tissue, biting (firing the needle), tensioning, and releasing the suture. For completing knots, the process of approaching and biting the tissue is executed twice in the same place to form a tie and lock the knot into place. For completing the running stitches, STAR only executes one round of approaching the tissue, biting, tensioning, and releasing. For each suture, a maximum tension force of 2 N or a tension distance of 20 cm (dropping by 5 mm after each stitch) was implemented to guarantee a uniform suture tension without tearing the tissue.

The process of initial data collection for confidence level evaluation and model fitting are described. A variation of this process determining which sutures can be performed autonomously and which possibly require human intervention is implemented in real-time and described further below.

Figures 4B, 4C, 4D:
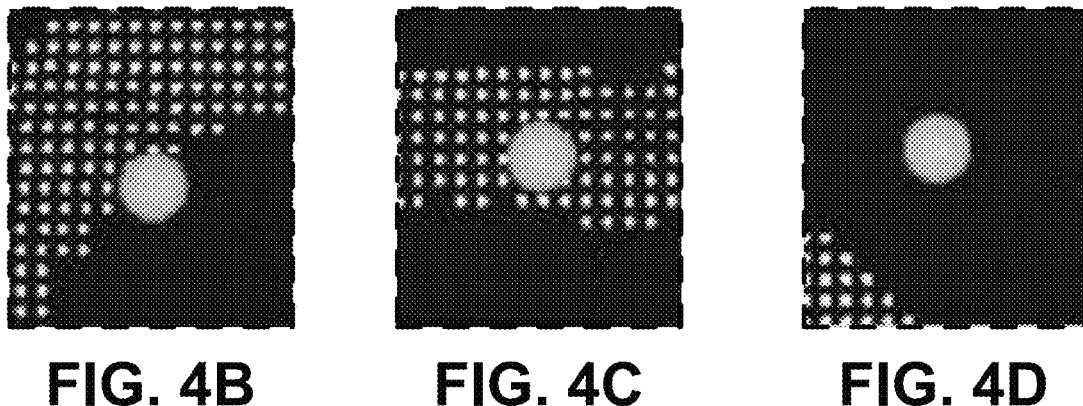
Figure 4E:
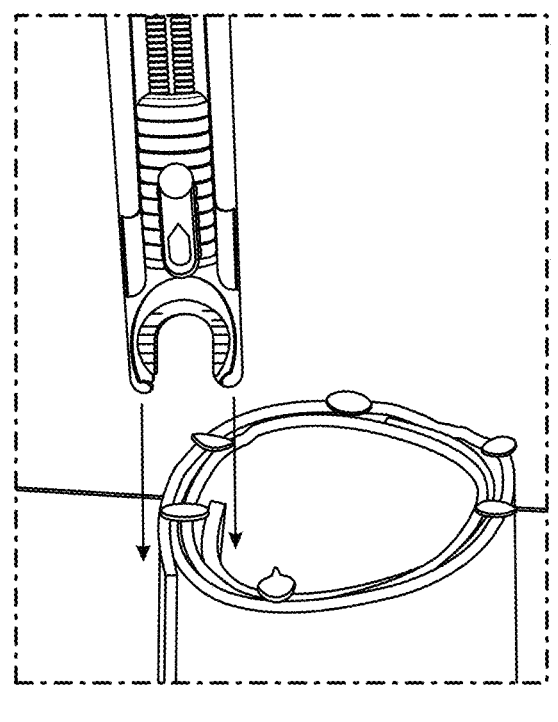
Figure 4F:
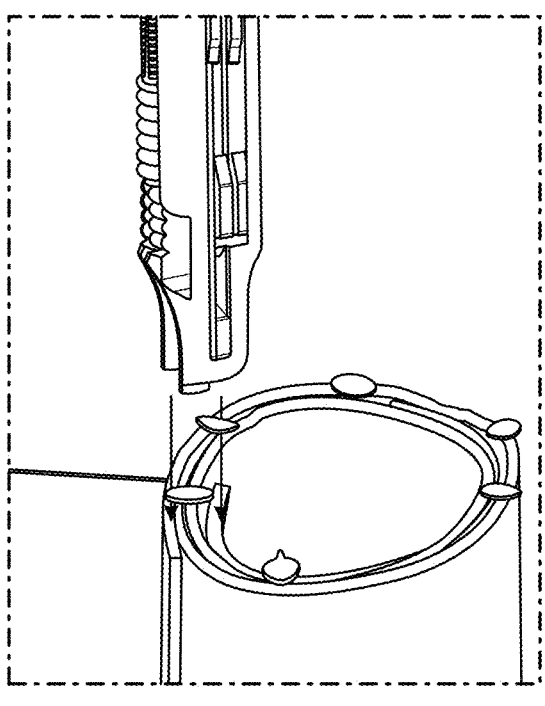
Figure 4G:
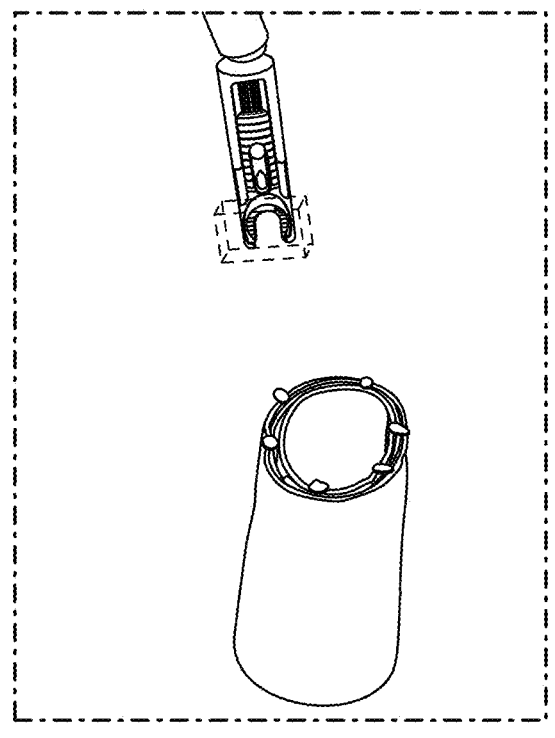
Figure 4H:
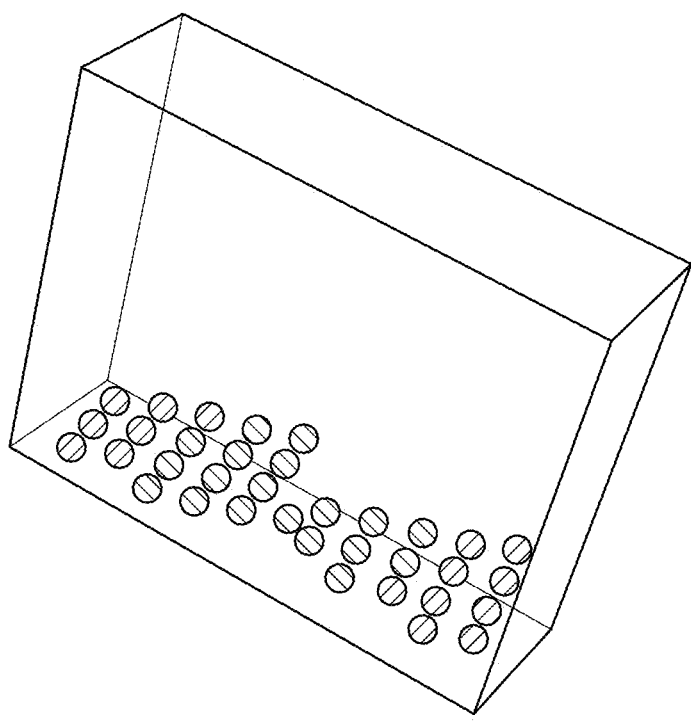
Figure 4I:
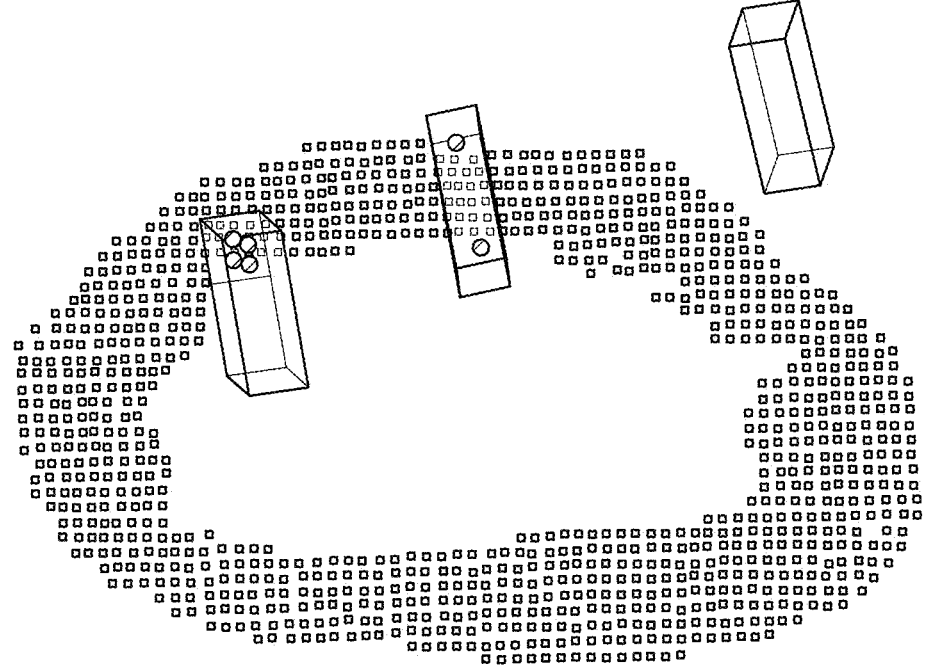

FIG. 4A, FIG. 4B, FIG. 4C, FIG. 4D, FIG. 4E, FIG. 4F, FIG. 4G, FIG. 4H, and FIG. 4I show examples of reaching suture points on a phantom vaginal cuff and steps of the data collection, according to examples of the present teachings, where FIG. 4A shows point cloud view with three suture points selected, FIG. 4B shows a suture point is on an edge, FIG. 4C shows a suture point has a high chance to be caught, FIG. 4D shows a suture point has no chance to be caught, FIG. 4E shows a good orientation of a tool-tip to reach suture points, FIG. 4F shows a bad orientation of the tool-tip to reach suture points, FIG. 4G shows rectangular box model of tool-tip, FIG. 4H shows the projected rectangular box containing Point-on-Tool (POT) (points 404) and PIJ (points 406), and FIG. 4I shows projected rectangular boxes to collect data on multiple suture points. The POT is a number that indicates how many tissue points are projected on the suturing tool. The higher the POT, the more likely the collision will happen as the suturing tool approaches the tissue.

Figure 5A:
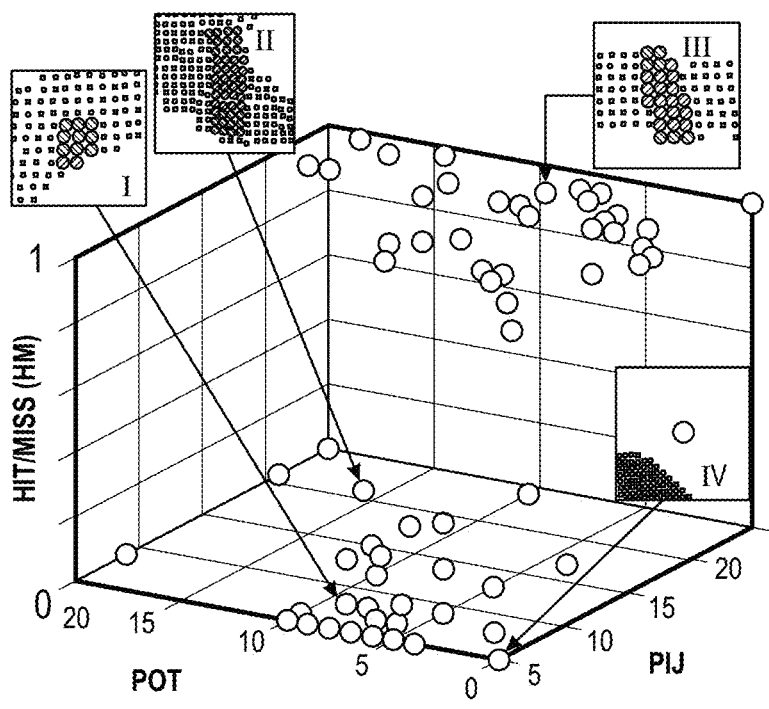
FIG. 5A and FIG. 5B show results of data collection and confidence model identification, according to examples of the present teachings.
Figure 5B:
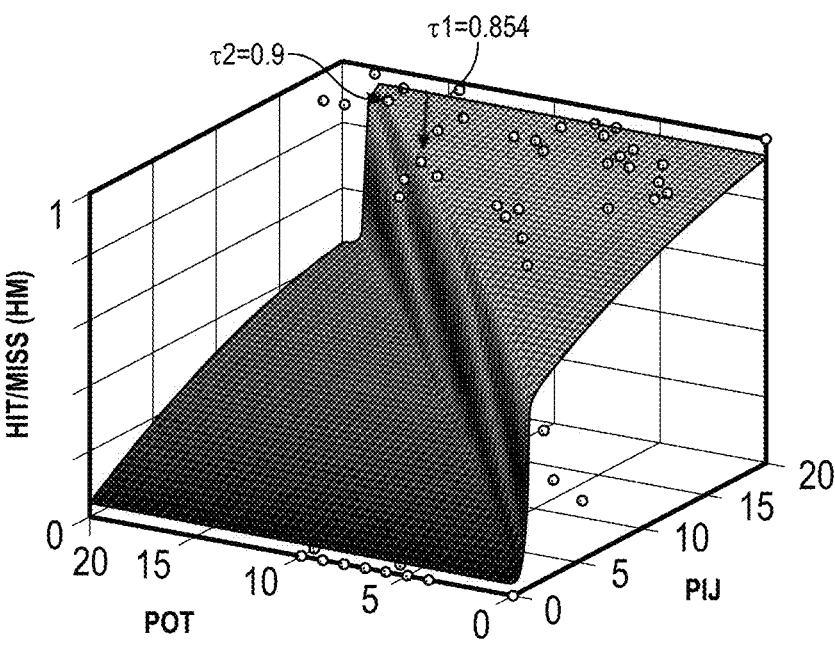

FIG. 5A and FIG. 5B show results of data collection and confidence model identification, according to examples of the present teachings. In FIG. 5A, data point examples of a.I) high POT but low PIJ, a.II) high POT and high PIJ, a.III) low POT but high PIJ, and a.IV) no POT and no PIJ. FIG. 5B shows the confidence model identified for the hit/miss based on collected data.

One factor affecting the correct suture placement that was discovered by the inventors in a prior study is whether the location of a new suture point was accurately estimated on an actual tissue for a robot to successfully reach. FIG. 4A shows an example of a planning scene with new suture points updated by the planner. The suture point in FIG. 4B is placed on the inside edge of the vaginal cuff, which indicates a lower chance for the needle to successfully catch the tissue. The suture point shown in FIG. 4C, has a higher chance for a stitch to be placed successfully since its location is in middle from both side of the tissue. The suture point placed on empty area in FIG. 4D has no chance for the robot to complete a stitch since no physical target is present at the target location.

In addition to how accurately the suture point is estimated by the planner, the geometry of the suture tool also affects the chance of successfully reaching the target. If the tissue portion appears more in the needle jaw as the suturing tool approaches the target, as shown in FIG. 4E, the suture tool has a higher chance to catch the target, and vice versa (FIG. 4F). A hypothesis tested by the inventors is that the robot confidence for placing a stitch successfully on a suture point is associated with tissue information near the suture point, and the geometrical information of the tool-tip projected at the suture point. After collecting this information, an identification process will be carried out to determine a confidence model. In the real-time experiments, the resulting model is used to evaluate the confidence level for success in completing a stitch on a suture point and hence autonomy allocation. Next, the data collection process for the model identification is described.

In the data collection step, the point cloud near a target location within a region is collected based on the geometrical information of the suture tool-tip. A vaginal cuff phantom tissue is used as a target and is placed in the dual camera view (FIG. 4G). The robot is first commanded to reach a target location which is manually selected from the RGBD camera view through a software interface. A rectangular box is defined, shown by 402 in FIG. 4G, with the same dimensions (10 mm×3 mm×8 mm) of the needle jaw and collect point cloud within the box using a passthrough filter in Point Cloud Library (PCL). The orientation of the box is assigned with an identical orientation of the actual tool-tip with respect to the robot base frame. As used herein, PIJ are point cloud points that are projected to be within the tool jaw if the tool moves exactly to the suture position and POT are the counterpart points that are projected to collide with the tool jaws. The collected point cloud in the box are categorized into two groups (FIG. 4H): points in jaw (PIJ), shown as points 406, and points on tool (POT), shown as points 404. The boxes are used to collect the PIJ and POT on the selected locations, shown in FIG. 4I. An additional information of whether the robot hits or misses (HM) is recorded by commanding the robot to reach each target location and visually examining whether the needle penetrates the target. The data is evaluated through MATLAB (MathWorks, Natick, MA, USA) to find a confidence model.

FIG. 5A shows the result of the data collection process. A total of 94 data points were collected by using the methods described in section II-D. Each data point encapsulates three sets of information: PIJ, POT, and HM. Notice that the resolution of point cloud in an area can be affected by how far the target is placed away from the RGBD camera. In the experiments conducted by the inventors, the target tissue was located within a 35-38 cm distance from the RGBD camera which satisfies minimum sensing distance of the camera as well as sufficient workspace for the robot to operate. In FIG. 5A, both axes were cut off at 20 since there are no more than 20 points observed in each categories under chosen camera distance.

The HM data is plotted with 0 representing a miss and 1 representing a hit. Examples of individual data points are shown in the in FIG. 5A. FIG. 5A.I shows data points with low PIJ which indicate low chances for robot to place suture in the correct location. Data points with high PIJ and high POT, as shown in FIG. 5A.II, result in a similar number of hit and miss because the data could be on a flat surface (resulting in a collision or miss) or a narrow opening on the tissue which is not detected by the camera but is feasible for the robot to reach (resulting in a hit). Data points with high PIJ but low POT, shown in FIG. 5A.III, contain more successful targeting cases (i.e. HM=1). With most PIJ estimated in the jaw only, a tool-tip has a higher chance to fit the target inside the jaw and avoid tool collision. Lastly, data points with extremely low PIJ and low POT in FIG. 5A.IV mostly indicate the robot will fail to reach the target (i.e. HM=0).

The selection of the confidence model and autonomy allocation function $\alpha$ is now discussed. Using the data collected from the data collection process, the robot performance is analyzed based on PIJ and POT to identify a confidence model. The curve fitting toolbox in MATLAB was used and multiple curves were fitted to the collected data with x=PIJ, y=POT, and $c_a$=HM (i.e. the confidence in autonomous control). First order to third order combinations of x and y are examined and eventually variables x−y, x, and $x^2$ were chosen for candidate inputs to the model fits of data because of their strong positive relationship to $c_a$ (i.e., correlation coefficient R>0.6). FIG. 5B shows results of a best fitted model which describes the data behavior according to the following $$c_a = a + \frac{b}{e^{-c(x-y-d)}} + gx + hx^2$$

with a=0.031, b=0.518, c=10.68, d=1.033, g=0.032, and h=−0.0007. According to FIG. 5B, the fitted function suggests that the chance of the robot hitting a target suture point increases when the difference between PIJ and POT increases and vice versa. Similarly, more/less PIJ results in higher/lower chance of reaching a perfect suture location. The fitted curve in FIG. 5B is defined as a confidence model for the robot (i.e., autonomous mode) performance.

An autonomy allocation function $\alpha$ can be determined once the confidence model is defined. The autonomy allocation function serves as a switch to indicate if a task is autonomous ($\alpha$=0), or manual/assisted ($\alpha$=1) based on the confidence model and a decision threshold $\tau$. In an actual suturing task, an estimated HM chance of a planned suture point can be derived by mapping its PIJ and POT onto the confidence model. If the estimated HM lies beyond the threshold, the autonomy allocation function considers the robot is confident to accomplish the task autonomously ($\alpha$=0 when $c_a \geq \tau$). On the other hand, if the estimated HM falls under the confidence threshold, the autonomy allocation function believes the robot needs supervision when performing tasks ($\alpha$=1).

In the experiments conducted by the inventors, two thresholds were chosen $\tau_1$=0.854, $\tau_2$=0.9 for the disclosed system to perform vaginal cuff closure in the experiments. The first threshold $\tau_1$=0.854 was chosen after performing pure autonomous targeting tests on vaginal cuff phantom with different open and close samples under rotated configurations (0°, 15°, and −15°), evaluating how many target points were successfully reached. In the test, 41 target points were hit out of total 48. Thus, the success rate 0.854 (85.4%) was chosen as the first decision threshold. The second decision threshold $\tau_2$ was selected through confidence model in FIG. 5B. To maximize robot performance in terms of accuracy, $\tau_2$=0.9 was selected to be the decision threshold in the figure (i.e., success rate of 90% or higher as a decision threshold). It is expected that the allocation function with a 90% threshold will be more conservative and will assign more tasks to the operator for supervising autonomous mode. The decision thresholds $\tau_1$ and $\tau_2$ were used by STAR in the final experiments.

TABLE I

| | Comparison of robotic and manual results. | | | |
|---|---|---|---|---|
| Modality | Total Time (min) | Time per stich (sec) | Suture Spacing (mm) | Bite Size (mm) |
| STAR | 17.7 ± 0.7 | 88.9 ± 23.2 | 7.41 ± 1.33 | 5.71 ± 1.34 |
| Manual [24] | 6.9 ± 0.2 | 19.5 ± 3.8 | 9.19 ± 2.08 | 4.96 ± 2.39 |

13

TABLE II

Comparison of first attempt hit and misses based on
the decision threshold ($\tau_1$ = 85.4% and $\tau_2$ = 90.%
confidence levels) for a total 52 suture placements.

| | Predicted/Suggested Mode | | | | | |
| | Auto | | | Assisted | | |
| | $\tau_1$ | $\tau_2$ | All | $\tau_1$ | $\tau_2$ | all |
|---|---|---|---|---|---|---|
| Hit | 12 | 6 | 18 | 10 | 11 | 21 |
| Miss | 1 | 0 | 1 | 3 | 9 | 12 |
| Total | 13 | 6 | 19 | 13 | 20 | 33 |

C. Results of Vaginal Cuff Closure

Figure 6A:
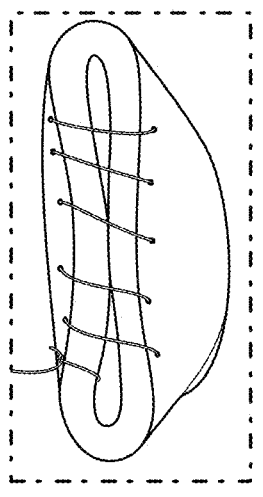
FIG. 6A, FIG. 6B, FIG. 6C, and FIG. 6D show results of synthetic vaginal cuff closure according to examples of the present teachings, where
Figure 6B:
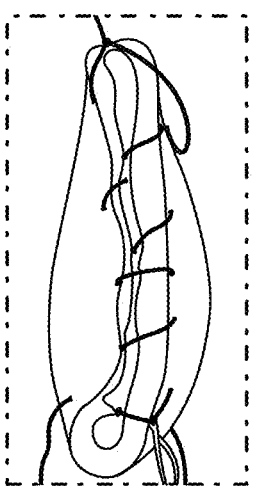

Four robotic suturing experiments were conducted on vaginal cuff phantoms using STAR with the disclosed method. STAR performed two suturing tasks for each decision threshold $\tau_1$ and $\tau_2$. Each task included completing a knot at the beginning followed by 11 running stitches and autonomous tensioning. The suturing results done by STAR and by manual method is first compared. The results of the robotic and manual suturing are summarized in Table I. Representative results of robotic and manual suturing are shown in FIG. 6A and FIG. 6B. In Table I, the task completion time for STAR is on average 10.8 minutes (647 seconds) longer and is on average 69.4 seconds slower in completing a stitch than the surgeon. Regarding the suture spacing and bite size, variance of both modalities are statistically less for STAR compared to that of the manual results (p<0.05), which indicates STAR can place the running stitches more uniformly (1.6 times better) and is more consistent in bite depth (1.8 times better) compared to the surgeon.

Figure 6C:
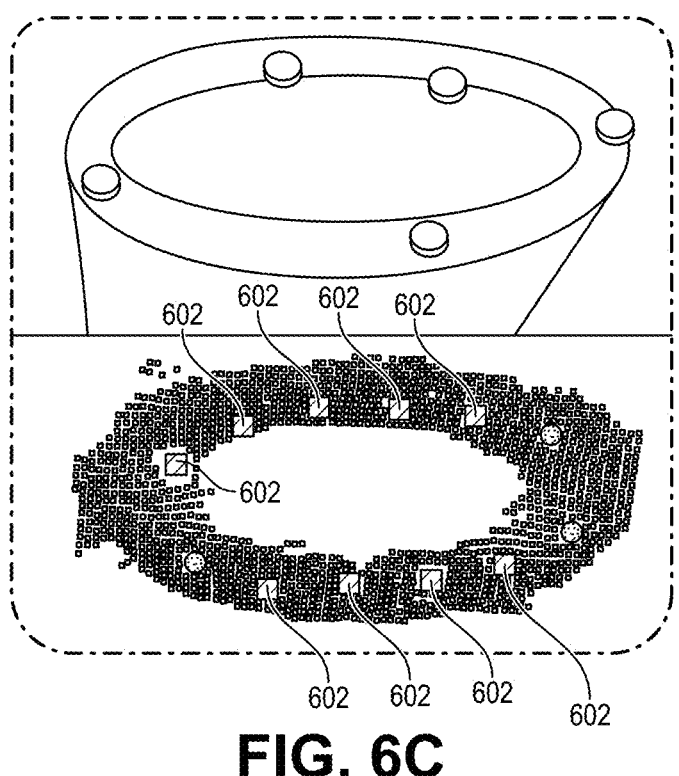
Figure 6D:
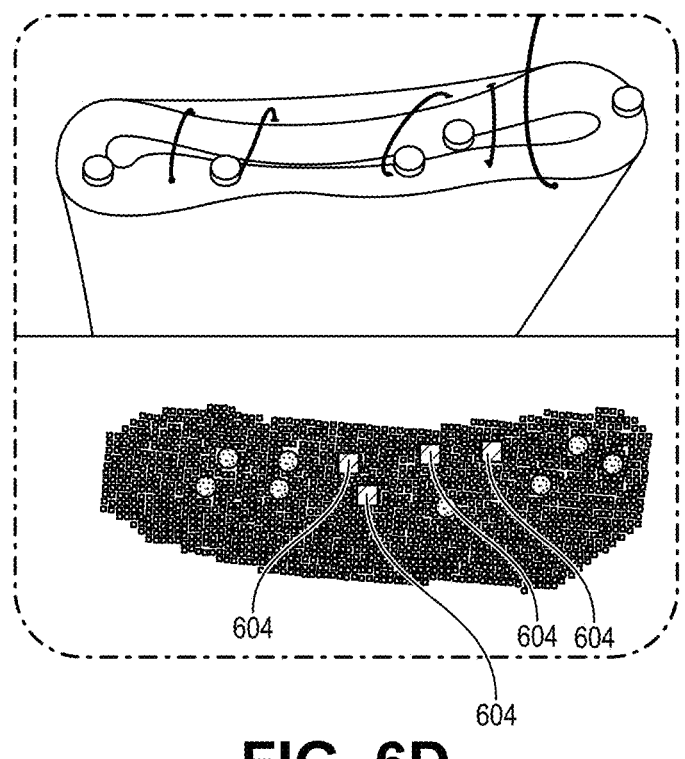

FIG. 6A, FIG. 6B, FIG. 6C, and FIG. 6D show results of synthetic vaginal cuff closure according to examples of the present teachings, where FIG. 6A shows STAR, FIG. 6B shows manual [24], FIG. 6C shows a higher number of suture points 602 before suturing, and FIG. 6D shows a lower number of suture points 604 after the vaginal cuff is closed.

Figure 7A:
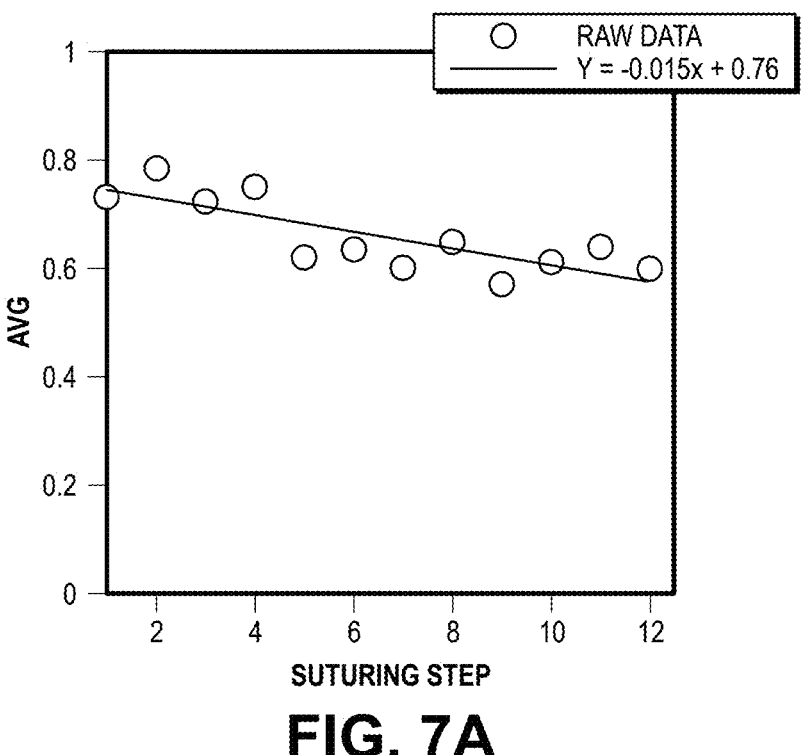
FIG. 7A show a plot of average of confidence in autonomous suturing versus task progressions and FIG. 7B shows a plot of standard deviation of confidence in autonomous suturing versus task progressions, according to examples of the present teachings.
Figure 7B:
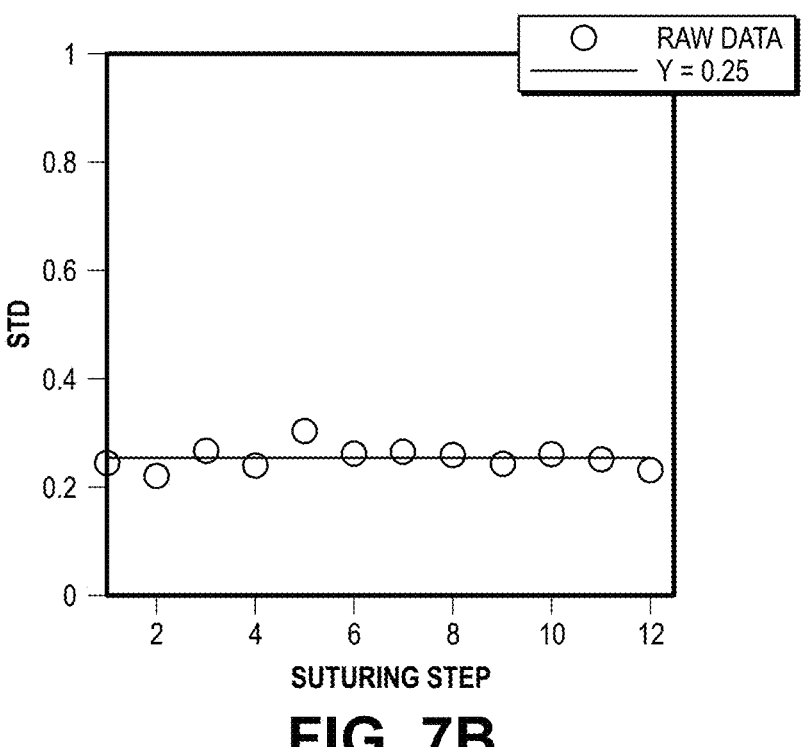

FIG. 7A show a plot of average of confidence in autonomous suturing versus task progressions and FIG. 7B shows a plot of standard deviation of confidence in autonomous suturing versus task progressions, according to examples of the present teachings.

From the results in Table II, it can be seen that the less conservative decision threshold $\tau_1$=85.4% resulted in higher number of autonomous suture placement compared to $\tau_2$=90% (i.e. 117% more considering total suggestions of 13 vs 6). However, $\tau_2$ resulted in 100% successful hits compared to the 92.31% hit rate via $\tau_1$, both of which were greater than the chosen thresholds. For the total of 19 predicted autonomous sutures, the prediction accuracy was 94.74% (i.e., 18 correct out of 19 guesses). The missed stitch occurred at the 11th suture of the test which is very close to the final steps of the suturing process when the target tissue is almost closed and generally with a higher risk of missing an autonomous suture. This can be verified via the plots in FIG. 7 that show how the average predicted confidence in autonomous suture placement degrades closer to the end of the suturing task during the 4 tests. A representative example is shown in FIG. 6C and FIG. 6D, which can differentiate the easy and difficult parts of the suturing via the generally higher and lower number of green suturing points (i.e., the points that robot is confident in performing an autonomous suture placement). In these experiments 45.16% of the manual/assisted control suggestions happened in the first half of the suturing task (generally easier since the tissue is more open and approachable by the robot) and 54.84% in the second half (i.e., ratio of 0.82).

From the total of 33 sutures predicted in the manual/assisted mode, which warned the operator about the possibility of missing a stitch in the correct location, 12 stitches really required human intervention (i.e., 36.36% of the suggested stitches). This happens because relatively high confidence levels for the decision threshold was selected to guarantee a higher accuracy. Furthermore, based on the initial data collection and confidence model-fitting, it is known that a miss is guaranteed only for suture points with very low confidence levels in the autonomous mode. Therefore, these conservative predictions still provide valuable feedback for alerting the operator in the assisted mode to supervise the robot for possible misses and a need for tool-tip position corrections. In these tests, for the sutures that required operator assistance, an average of 3.99±1.02 mm offsets were implemented via the GUI to ensure the suture is placed in the correct location. For the total of 52 stitches placed using the confidence-based method, a total of 25% required human intervention (i.e., 12 missed stitches from the predicted assisted sutures and 1 miss from the predicted autonomous sutures).

Figure 8A:
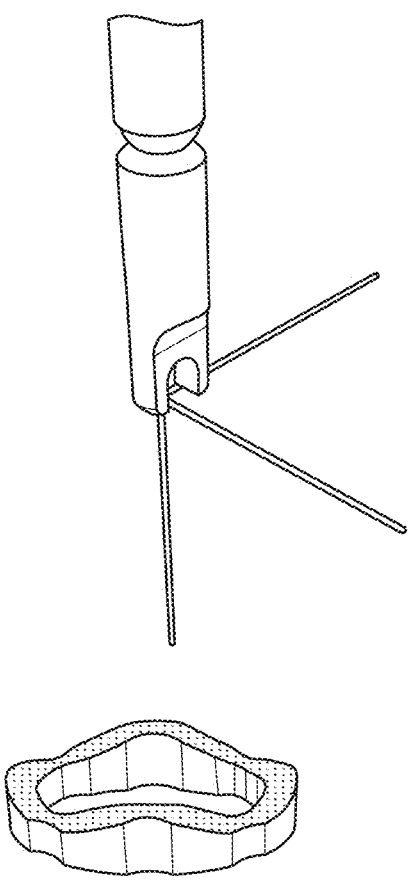
FIG. 8A shows an orientation assigned to the projected bounding box is the orientation of the suturing tool according to examples of the present disclosure.
Figure 8B:
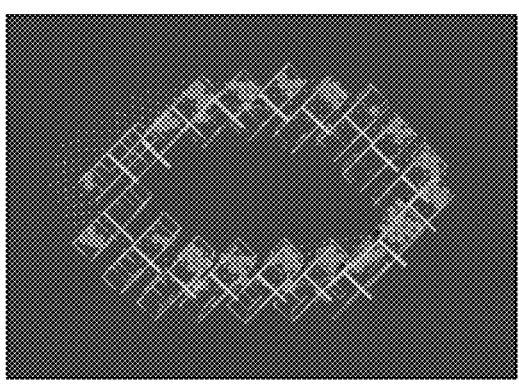
FIG. 8B shows a problem where no path orientation is considered, and a planning result contains large POT when projecting bounding boxes to a suture path according to examples of the present disclosure.
Figure 9A:
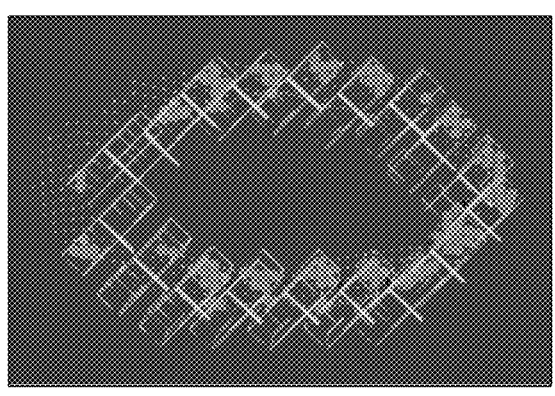
FIG. 9A, FIG. 9B, FIG. 9C, and FIG. 9D show the planning results on POT with each planning method associated to the suturing tool configurations (angle changed on Yaw) according to examples of the present disclosure.
Figure 9B:
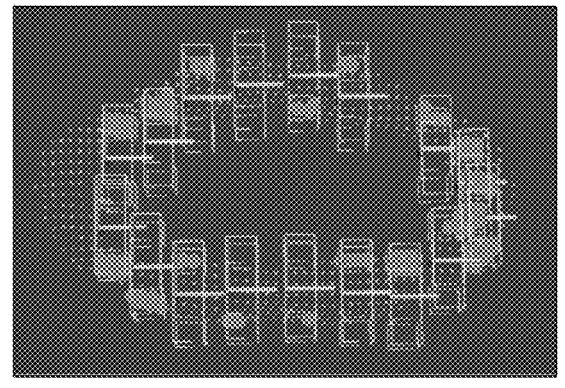
Figure 9C:
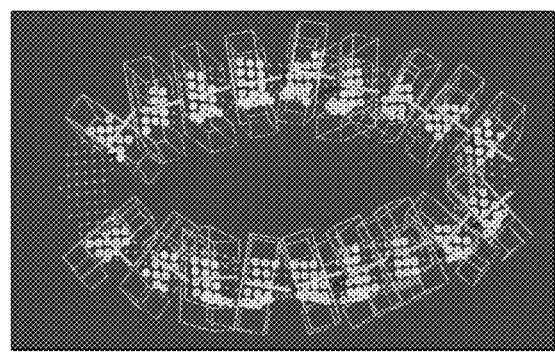
Figure 9D:
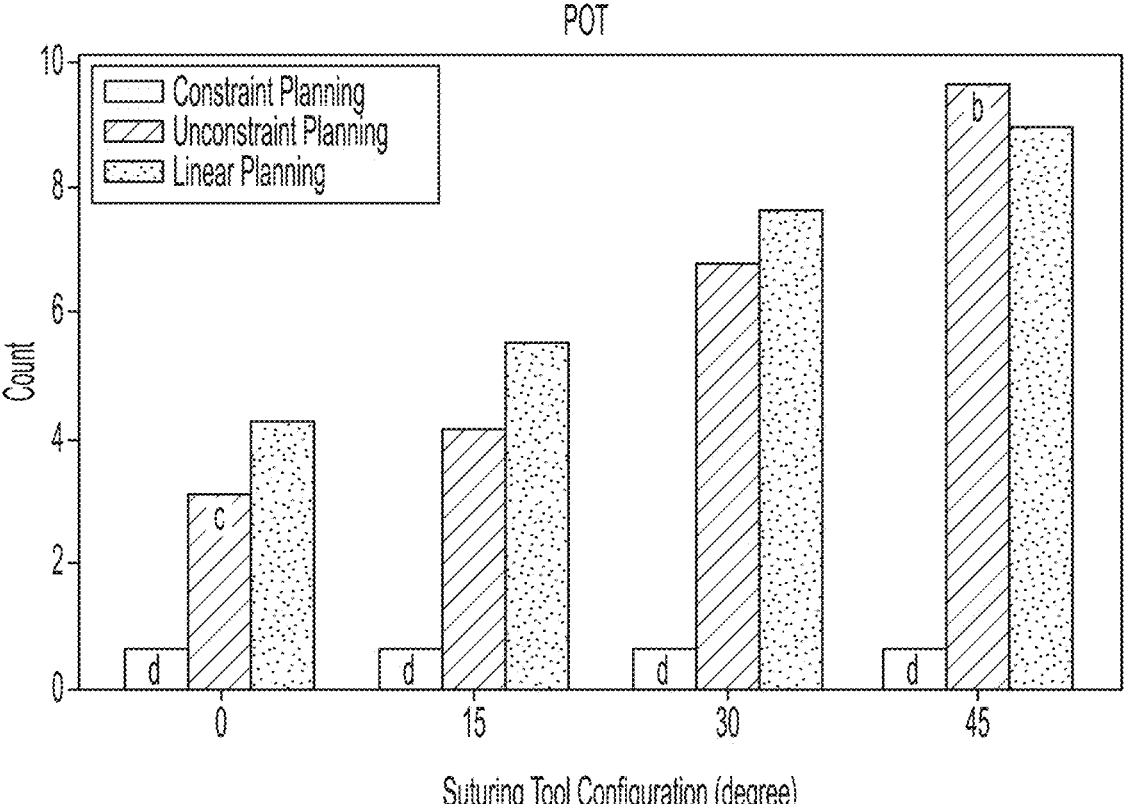

In the current suture planning method, a path planner generates the shortest path via point cloud path planning between markers and distributes suture points with or without equal spacing along the path. However, the planned suture points only contain position information (i.e., x, y, and z) without the changes of orientation when suturing along the path. FIG. 8A shows an orientation assigned to the projected bounding box is the orientation of the suturing tool according to examples of the present disclosure. FIG. 8B shows a problem where no path orientation is considered, and a planning result contains large POT when projecting bounding boxes to a suture path according to examples of the present disclosure. As the robot controller takes a wrong orientation of the suturing tool to approach the suture point, the collision between the tissue and tool is likely to fail placing a stitch.

Taking path orientation into account for suture planning reduces the POT of the suture plan and infers increasing the confidence of autonomous suturing. A constraint suture planning method is used that constructs the rotation basis of each suture point to reduce POT when planning on different tissue configurations. For each suture point, the method computes direction (i.e., unit vector) to the next-neighboring suture point as a y rotation basis. The rotation component on z is determined by the normal vector of a plane estimated via least squares fitting to all suture points. Lastly, the rotation component on x is computed via a cross-product of y and z axes. The orientation on each suture point can be utilized by the robot controller to orient the suturing tool and place stitches with success.

FIG. 9A, FIG. 9B, FIG. 9C, and FIG. 9D show the planning results on POT with each planning method associated to the suturing tool configurations (angle changed on Yaw) according to examples of the present disclosure. A vaginal cuff tissue phantom was used as a planning scene in a simulation environment. A total of three planning methods (linear, unconstraint planning, and constraint planning) were evaluated by POT on each suture plan. The planning result of the disclosed constraint method shows the advantage of reducing POT in average 10.53 times and 9.43 times on that of linear and unconstraint planning methods. The constraint planning method generates a plan with consistent and lowest POT regardless of tool configurations. In other words, the planning method can compute and adjust the suture plan autonomously even the change of planning scene. The robot controller can access the new suture plan without readjustment on the configuration of the suturing tool. In contrast, the POT on the planning results by linear and unconstraint planning change dramatically depending on the orientation of the suturing tool. The suture plan without path orientation is sensitive to tool configuration when the planning scene has changed and, therefore, multiple readjustments of the suturing tool configuration are needed to reduce the POT.

Figures 10A, 10B:
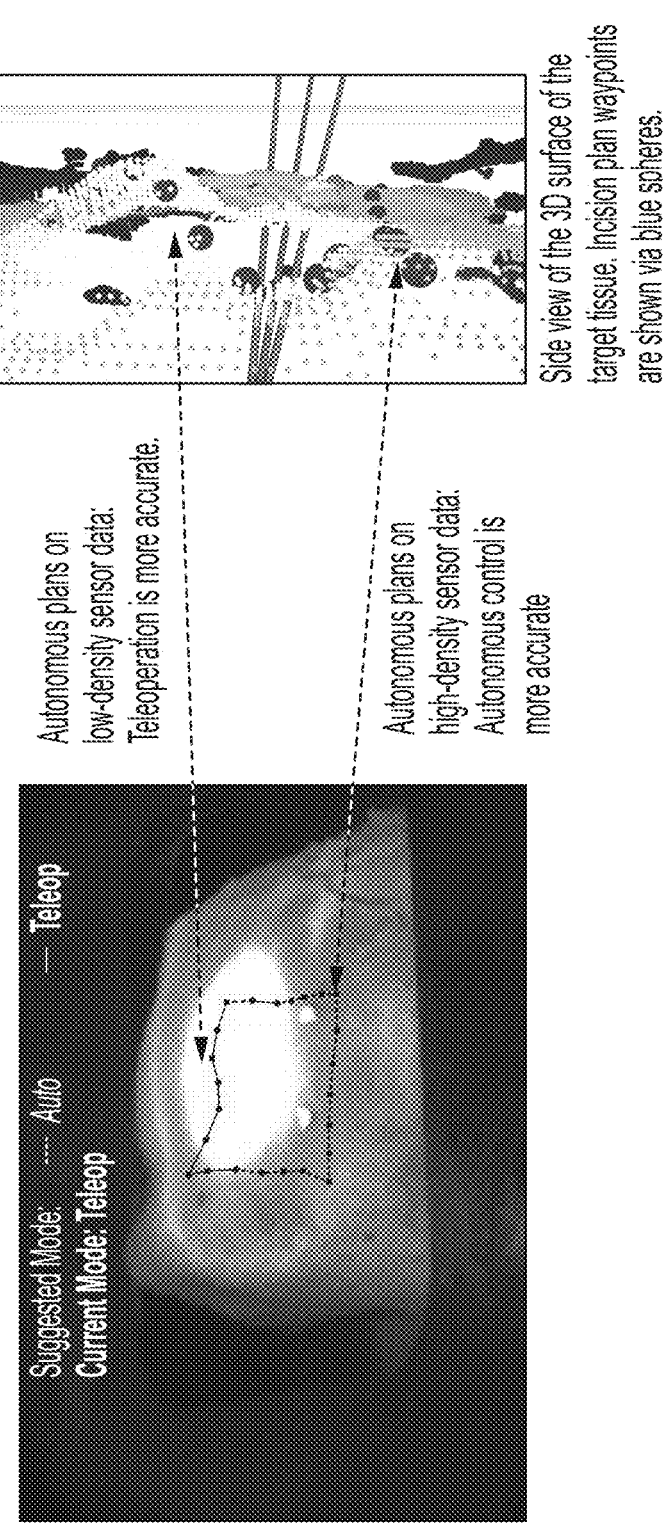
FIG. 10A shows a user interface for a confidence-based robotic electrosurgery with a binary control allocation method according to examples of the present disclosure.
FIG. 10B shows a side view of the 3D surface of the target tissue, incision plan waypoints for the electrosurgery of FIG. 10A.

FIG. 10A shows a user interface for a confidence-based robotic electrosurgery with a binary control allocation method according to examples of the present disclosure. FIG. 10B shows a side view of the 3D surface of the target tissue, incision plan waypoints for the electrosurgery of FIG. 10A. A realization of the user interface for confidence-based robotic electrosurgery with a binary control allocation method (switches between teleoperation and autonomous control mode) is further described. Via this method, autonomous plans in the regions with noisy data and low sensor data density result in a lower confidence in autonomous control and vice versa. Therefore, the robotic system provides a teleoperation mode when the confidence to autonomous control drops below a threshold. Otherwise (when the confidence in autonomous control is above a threshold) autonomous control is provided.

FIG. 11A, FIG. 11B, and FIG. 11C show smooth transitions between control modes according to examples of the present disclosure. FIG. 12A and FIG. 12B show additional examples of smooth transitions between control modes according to examples of the present disclosure. In order to realize smooth transitions between from the autonomous control to the teleoperation mode via a haptic control device, the following methods are implemented. A non-linear dead zone with scaling is applied around the haptic device origin (where a pure zero teleoperation command is defined). The dead zone guarantees that slight motions and local drifts of the operator hand do not cause a sudden jump (non-zero command) when switching from the autonomous to teleoperation mode. Scaling the operator command adds additional safety measures during the transition. An additional gravity compensation force is applied on the control device to help the operator remove the undesired downward commands resulting from the weight of operator's hand on the control device. For smooth transitions from teleoperation mode to autonomous mode, the autonomous trajectory generation algorithms will continuously track the operator commands in the teleoperation and use them as a starting point for the autonomous control commands once the control transition is complete.

FIG. 13 shows a flowchart for a computer-implemented method 1300 for robot-assisted suturing, according to examples of the present teachings. The computer-implemented method 1300 comprises determining, by a suture planner algorithm executed by a hardware processor, a desired location for a suture for a potential suture location on a treatment area on a patient, as in 1302. In some examples, the desired location of one or more sutures points is modifiable by activation of a graphical selection tool on a graphical user interface (GUI), by textual input on the GUI, or by a haptic user interface. In some examples, the graphical selection tool comprises a slider, a pointer, a button, a multi-axis master control device, or combinations thereof. In some examples, the one or more sutures points are color-coded on the GUI.

In some examples, the determining the desired location comprises obtaining, by the hardware processor, a 3D position of landmarks for planning the potential suture location imaged by a 3D sensing system, as in 1304. In some examples, the computer-implemented method 1300 further comprises determining, by the suture planner algorithm and each of the landmarks and a point could, a desired location for each suture, as in 1306. In some examples, the determining the desired location for suture, for example, each knot and the running stitch, comprises using a point cloud path planning method to initiate a suture plan based on positions of the landmarks and using a non-rigid registration method for updating a new suture plan on a deformed tissue during the suturing, as in 1308.

The computer-implemented method 1300 continues by determining which sutures from the suture planner algorithm can be done autonomously and which sutures may require human intervention to be performed, as in 1310.

In some examples, the computer-implemented method 1300 further comprises providing a representation of the treatment area being sutured on a graphical user interface (GUI) that allows a user to modify one or more suture points on the GUI if an initial semi-autonomous suture placement results in a misplaced suture, as in 1312.

In some examples, the computer-implemented method 1300 further comprises receiving, at a task planner algorithm, 3D coordinates of the suture points in the robot frame from the suture planning algorithm and planning, by the task planner algorithm, a sequence of robot motions to complete the suturing using desired and planned positions, as in 1314. In some examples, the sequence of robot motions comprises motions representing approaching tissue at the treatment area, motions representing biting or firing a needle, motions representing tensioning the suture, or motions representing releasing the suture.

As discussed above, the disclosed confidence-based method takes a more conservative approach toward autonomous suture placement and hence increases the accuracy of autonomous suture placements from 85.4% in a pure autonomous suturing process to 94.74%. For the overall 52 suture placement attempts during the 4 tests, this accuracy is 98.1% by taking advantage of a 25% overall human intervention. However, this rate of intervention is considerably smaller compared to the case where a human needs to manually adjust all the sutures via the same robotic system without any use of autonomy. In some examples, the disclosed confidence-based strategy can further include additional confidence measures, such as the accuracy of the system calibration, non-uniform weighting for the PIJ and POJ points based on distance to the tool center, proximity of NIR markers and consecutive suture points, which may further improve the accuracy of the predictions. Moreover, a 3D camera with a higher resolution can be included that may improve the accuracy of point cloud-based estimations.

In summary, a supervised autonomous suturing method is disclosed that enables STAR to perform confidence-based suturing task collaboratively with operators. Specifically, a confidence model as well as an allocation function were identified based on the point cloud information of the tooltip. STAR performs autonomous suturing with the disclosed method to predict whether it is confident to place a stitch successfully on a suture point or needs a positioning adjustment from the operator. The results demonstrate that with using the disclosed confidence model, STAR can predict the success of pure autonomous fairly accurately as well as improve suture placement accuracy over pure autonomous control. Moreover, STAR achieves results with better consistency in suture spacing and bite size compared to the manual laparoscopic surgery.

Figure 14:
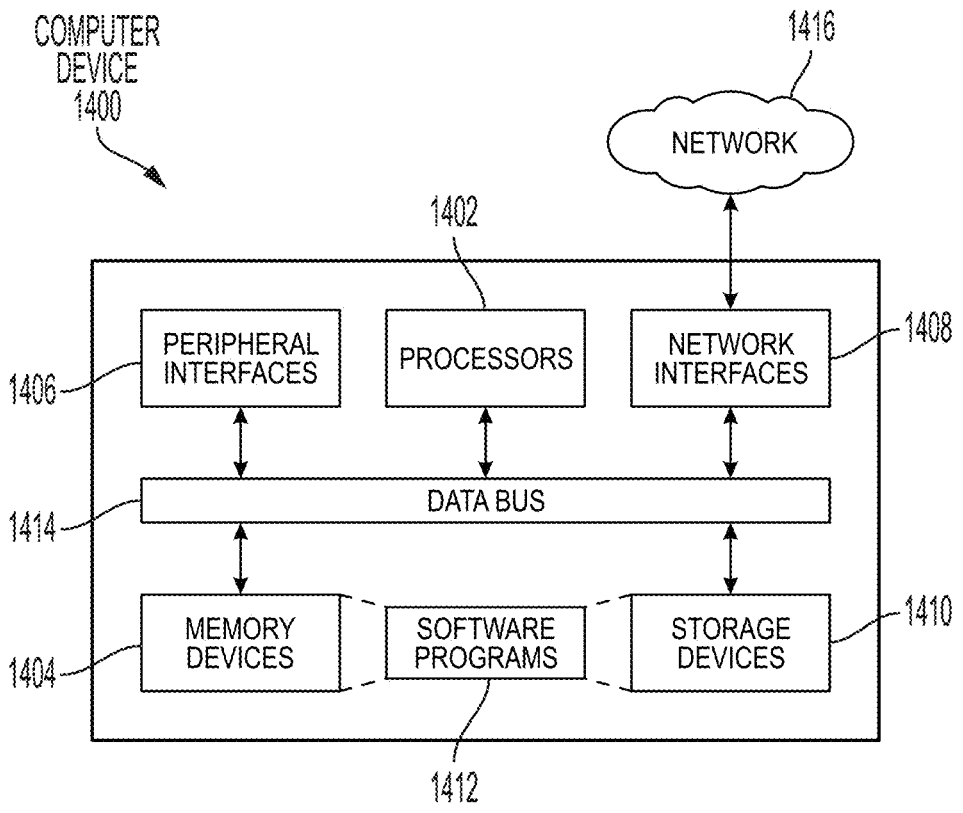
FIG. 14 shows a computer system for performing the disclosed methods according to examples of the present teachings.

FIG. 14 is an example of a hardware configuration for computer device 1400, which can be used to perform one or more of the processes described above. Computer device 1400 can be any type of computer devices, such as desktops, laptops, servers, etc., or mobile devices, such as smart telephones, tablet computers, cellular telephones, personal digital assistants, etc. As illustrated in FIG. 14, computer device 1400 can include one or more processors 1402 of varying core configurations and clock frequencies. Computer device 1400 can also include one or more memory devices 1404 that serve as a main memory during the operation of computer device 1400. For example, during operation, a copy of the software that supports the above-described operations can be stored in one or more memory devices 1404. Computer device 1400 can also include one or more peripheral interfaces 1406, such as keyboards, mice, touchpads, computer screens, touchscreens, etc., for enabling human interaction with and manipulation of computer device 1400.

The computer device 1400 can also include one or more network interfaces 1408 for communicating via one or more networks, such as Ethernet adapters, wireless transceivers, or serial network components, for communicating over wired or wireless media using protocols. Computer device 1400 can also include one or more storage devices 1410 of varying physical dimensions and storage capacities, such as flash drives, hard drives, random access memory, etc., for storing data, such as images, files, and program instructions for execution by one or more processors 1402.

Additionally, computer device 1400 can include one or more software programs 1412 that enable the functionality described above. One or more software programs 1412 can include instructions that cause one or more processors 1402 to perform the processes, functions, and operations described herein, for example, with respect to the processes of FIG. 13. Copies of one or more software programs 1412 can be stored in one or more memory devices 1404 and/or on in one or more storage devices 1410. Likewise, the data utilized by one or more software programs 1412 can be stored in one or more memory devices 1404 and/or on in one or more storage devices 1410. Data bus 1414 electrically and communicatively couples the various components of the computer device 1400.

In implementations, computer device 1400 can communicate with other devices via network 1416. The other devices can be any types of devices as described above. Network 1416 can be any type of network, such as a local area network, a wide-area network, a virtual private network, the Internet, an intranet, an extranet, a public switched telephone network, an infrared network, a wireless network, and any combination thereof. Network 1416 can support communications using any of a variety of commercially-available protocols, such as TCP/IP, UDP, OSI, FTP, UPnP, NFS, CIFS, AppleTalk, and the like. Network 1416 can be, for example, a local area network, a wide-area network, a virtual private network, the Internet, an intranet, an extranet, a public switched telephone network, an infrared network, a wireless network, and any combination thereof.

Computer device 1400 can include a variety of data stores and other memory and storage media as discussed above. These can reside in a variety of locations, such as on a storage medium local to (and/or resident in) one or more of the computers or remote from any or all of the computers across the network. In some implementations, information can reside in a storage-area network ("SAN") familiar to those skilled in the art. Similarly, any necessary files for performing the functions attributed to the computers, servers, or other network devices may be stored locally and/or remotely, as appropriate.

In implementations, the components of computer device 1400 as described above need not be enclosed within a single enclosure or even located in close proximity to one another. Those skilled in the art will appreciate that the above-described componentry are examples only, as computer device 1400 can include any type of hardware componentry, including any necessary accompanying firmware or software, for performing the disclosed implementations. Computer device 1400 can also be implemented in part or in whole by electronic circuit components or processors, such as application-specific integrated circuits (ASICs) or field-programmable gate arrays (FPGAs).

If implemented in software, the functions can be stored on or transmitted over a computer-readable medium as one or more instructions or code. Computer-readable media includes both tangible, non-transitory computer storage media and communication media including any medium that facilitates transfer of a computer program from one place to another. A storage media can be any available tangible, non-transitory media that can be accessed by a computer. By way of example, and not limitation, such tangible, non-transitory computer-readable media can comprise RAM, ROM, flash memory, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, includes CD, laser disc, optical disc, DVD, floppy disk and Blu-ray disc where disks usually reproduce data magnetically, while discs reproduce data optically with lasers. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Combinations of the above should also be included within the scope of computer-readable media.

The foregoing description is illustrative, and variations in configuration and implementation can occur to persons skilled in the art. For instance, the various illustrative logics, logical blocks, modules, and circuits described in connection with examples of the present disclosure disclosed herein can be implemented or performed with a general purpose processor, a digital signal processor (DSP), an application specific integrated circuit (ASIC), a field programmable gate array (FPGA), cryptographic co-processor, or other programmable logic device, discrete gate or transistor logic, discrete hardware components, or any combination thereof designed to perform the functions described herein. A general-purpose processor can be a microprocessor, but, in the alternative, the processor can be any conventional processor, controller, microcontroller, or state machine. A processor can also be implemented as a combination of computing devices, e.g., a combination of a DSP and a microprocessor, a plurality of microprocessors, one or more microprocessors in conjunction with a DSP core, or any other such configuration.

In one or more examples, the functions described can be implemented in hardware, software, firmware, or any combination thereof. For a software implementation, the techniques described herein can be implemented with modules (e.g., procedures, functions, subprograms, programs, routines, subroutines, modules, software packages, classes, and so on) that perform the functions described herein. A module can be coupled to another module or a hardware circuit by passing and/or receiving information, data, arguments, parameters, or memory contents. Information, arguments, parameters, data, or the like can be passed, forwarded, or transmitted using any suitable means including memory sharing, message passing, token passing, network transmission, and the like. The software codes can be stored in memory units and executed by processors. The memory unit can be implemented within the processor or external to the processor, in which case it can be communicatively coupled to the processor via various means as is known in the art.

Notwithstanding that the numerical ranges and parameters setting forth the broad scope of the present teachings are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 5. In certain cases, the numerical values as stated for the parameter can take on negative values. In this case, the example value of range stated as "less than 10" can assume negative values, e.g. $-1$, $-2$, $-3$, $-10$, $-20$, $-30$, etc.

While the present teachings have been illustrated with respect to one or more implementations, alterations and/or modifications can be made to the illustrated examples without departing from the spirit and scope of the appended claims. For example, it will be appreciated that while the process is described as a series of acts or events, the present teachings are not limited by the ordering of such acts or events. Some acts may occur in different orders and/or concurrently with other acts or events apart from those described herein. Also, not all process stages may be required to implement a methodology in accordance with one or more aspects or implementations of the present teachings. It will be appreciated that structural components and/or processing stages can be added or existing structural components and/or processing stages can be removed or modified. Further, one or more of the acts depicted herein may be carried out in one or more separate acts and/or phases. Furthermore, to the extent that the terms "including," "includes," "having," "has," "with," or variants thereof are used in either the detailed description and the claims, such terms are intended to be inclusive in a manner similar to the term "comprising." The term "at least one of" is used to mean one or more of the listed items can be selected. As used herein, the term "one or more of" with respect to a listing of items such as, for example, A and B, means A alone, B alone, or A and B. Further, in the discussion and claims herein, the term "on" used with respect to two materials, one "on" the other, means at least some contact between the materials, while "over" means the materials are in proximity, but possibly with one or more additional intervening materials such that contact is possible but not required. Neither "on" nor "over" implies any directionality as used herein. The term "about" indicates that the value listed may be somewhat altered, as long as the alteration does not result in nonconformance of the process or structure to the illustrated implementation. Finally, "exemplary" indicates the description is used as an example, rather than implying that it is an ideal. Other implementations of the present teachings will be apparent to those skilled in the art from consideration of the specification and practice of the disclosure herein. It is intended that the specification and examples be considered as exemplary only, with a true scope and spirit of the present teachings being indicated by the following claims.

What is claimed is:

1. A computer-implemented method for robot-assisted surgery, the computer-implemented method comprising:
    determining, by a suture planner executed by a processor, a desired location for a suture for a potential suture location on a treatment area on a patient; and
    determining which sutures from the suture planner can be done autonomously and which sutures may require human intervention to be performed,
    wherein the determining the desired location comprises obtaining, by the processor, a 3D position of landmarks for planning the potential suture location imaged by a 3D sensing system,
    wherein the determining the desired location comprises using a point cloud path planning method to initiate a suture plan based on positions of the landmarks and using a non-rigid registration method for updating a new suture plan on a deformed tissue during the suturing.

2. The computer-implemented method of claim 1, further comprising determining, by the suture planner and each of the landmarks and a point could, a desired location for each suture.

3. The computer-implemented method of claim 1, further comprising providing a representation of the treatment area being sutured on a graphical user interface (GUI) that allows a user to modify one or more suture points on the GUI, by textual input on the GUI, or by a haptic user interface if an initial semi-autonomous suture placement results in a misplaced suture.

4. The computer-implemented method of claim 1, further comprising receiving, at a task planner algorithm, 3D coordinates of the suture points in the robot frame from the suture planner and planning, by the task planner algorithm, a sequence of robot motions to complete the suturing using desired and planned positions.

5. The computer-implemented method of claim 4, wherein the sequence of robot motions comprises motions representing approaching tissue at the treatment area, motions representing biting or firing a needle, motions representing tensioning the suture, or motions representing releasing the suture.

6. The computer-implemented method of claim 1, wherein the desired location of one or more sutures points are modifiable by activation of a graphical selection tool on a graphical user interface (GUI).

7. The computer-implemented method of claim 6, wherein the graphical selection tool comprises a slider, a pointer, a button, a multi-axis master control device, or combinations thereof.

8. The computer-implemented method of claim 6, wherein the one or more sutures points are color-coded on the GUI.

9. A computer system comprising:

a processor;

a non-transitory computer readable medium comprising instructions that when executed by the processor perform a method for robot-assisted surgery, the computer-implemented method comprising:

determining, by a suture planner executed by a processor, a desired location for a suture for a potential suture location on a treatment area on a patient; and determining which sutures from the suture planner can be done autonomously and which sutures may require human intervention to be performed, wherein the determining the desired location comprises obtaining, by the processor, a 3D position of landmarks for planning the potential suture location imaged by a 3D sensing system, wherein the determining the desired location comprises using a point cloud path planning method to initiate a suture plan based on positions of the landmarks and using a non-rigid registration method for updating a new suture plan on a deformed tissue during the suturing.

10. The computer system of claim 9, wherein the method further comprises determining, by the suture planner and each of the landmarks and a point could, a desired location for each suture.

11. The computer system of claim 9, wherein the method further comprises providing a representation of the treatment area being sutured on a graphical user interface (GUI) that allows a user to modify one or more suture points on the GUI, by textual input on the GUI, or by a haptic user interface if an initial semi-autonomous suture placement results in a misplaced suture.

12. The computer system of claim 9, wherein the method further comprises receiving, at a task planner algorithm, 3D coordinates of the suture points in the robot frame from the suture planner and planning, by the task planner algorithm, a sequence of robot motions to complete the suturing using desired and planned positions.

13. The computer system of claim 9, wherein the desired location of one or more sutures points are modifiable by activation of a graphical selection tool on a graphical user interface (GUI).

14. The computer system of claim 13, wherein the graphical selection tool comprises a slider, a pointer, a button, a multi-axis master control device, or combinations thereof.

15. The computer system of claim 13, wherein the one or more sutures points are color-coded on the GUI.

16. A non-transitory computer readable medium comprising instructions that when executed by a hardware processor perform a method for robot-assisted surgery, the computer-implemented method comprising:

determining, by a suture planner executed by a processor, a desired location for a suture for a potential suture location on a treatment area on a patient; and determining which sutures from the suture planner can be done autonomously and which sutures may require human intervention to be performed, wherein the determining the desired location comprises obtaining, by the processor, a 3D position of landmarks for planning the potential suture location imaged by a 3D sensing system, wherein the determining the desired location comprises using a point cloud path planning method to initiate a suture plan based on positions of the landmarks and using a non-rigid registration method for updating a new suture plan on a deformed tissue during the suturing.

*    *    *    *    *